United States Patent
Han et al.

(10) Patent No.: US 6,465,432 B1
(45) Date of Patent: Oct. 15, 2002

(54) ISOLATED ANTIOXIDANT PEPTIDES FORM CASEIN AND METHODS FOR PREPARING, ISOLATING, AND IDENTIFYING ANTIOXIDANT PEPTIDES

(75) Inventors: Xiao-Qing Han, Naperville, IL (US); Kirk L. Parkin, Middleton, WI (US); Richard H. Lincourt, Mundelein; Song Gao, Glenview, both of IL (US)

(73) Assignee: Kraft Food Holdings, Inc., Northfield, IL (US)

( * ) Notice: Subject to any disclaimer, the term of this patent is extended or adjusted under 35 U.S.C. 154(b) by 0 days.

(21) Appl. No.: 09/650,429

(22) Filed: Aug. 28, 2000

(51) Int. Cl.[7] ............... A61K 38/00; A61K 47/00; C12P 21/06
(52) U.S. Cl. ............... 514/16; 514/12; 514/15; 514/17; 514/18; 424/439; 435/68.1; 426/34; 530/305; 530/329
(58) Field of Search ............... 424/439; 514/12, 514/15, 16, 17, 18; 530/305, 329; 435/68.1; 426/34

(56) References Cited

U.S. PATENT DOCUMENTS

| | | | |
|---|---|---|---|
| 5,250,513 A | | 10/1993 | N'Guyen et al. |
| 5,623,052 A | | 4/1997 | McLean et al. |
| 5,648,457 A | | 7/1997 | Takei et al. |
| 5,804,555 A | | 9/1998 | Tomita et al. |
| 5,840,485 A | * | 11/1998 | Lebl et al. ............... 435/6 |
| 5,846,939 A | * | 12/1998 | Miclo et al. ............... 514/15 |
| 5,952,193 A | | 9/1999 | Shimamura et al. |
| 6,022,702 A | | 2/2000 | Tsumura et al. |
| 6,036,983 A | | 3/2000 | Nielsen |
| 6,046,168 A | | 4/2000 | Kagawa et al. |
| 6,060,269 A | | 5/2000 | Chatterton et al. |
| 6,013,633 A | | 10/2000 | Balasubramanium et al. |

FOREIGN PATENT DOCUMENTS

| | | | | |
|---|---|---|---|---|
| JP | 06041191 | * | 2/1994 | ............ C07K/5/10 |
| JP | 06239888 | * | 8/1994 | ............ C07K/7/08 |
| WO | WO 92/15279 | * | 9/1992 | ............ A61K/7/48 |

OTHER PUBLICATIONS

Gutteridge et al., "Inhibition of lipid peroxidation by the iron–binding protein lactoferrin," Bioch, J., 199:259, 1981.
Laakso, "Inhibition of lipid peroxidation by casein: Evidence of molecular encapsulation of 1,4–pentadiene fatty acids," Biochim. Biophys. Acta 792:11 1984.
Suetsuna et al. "Isolation and characterization of free radical scavenging activities peptides derived from casein," J. Nurt. Biochem., 11:128, 2000.

* cited by examiner

Primary Examiner—Karen Cochrane Carlson
Assistant Examiner—Chih-Min Kam
(74) Attorney, Agent, or Firm—Fitch, Even, Tabin, & Flannery

(57) ABSTRACT

The current invention provides antioxidative peptide fractions. The invention includes antioxidative peptides of casein having sequences of SEQ ID NOS:1–5. The invention includes methods for making or generating the peptides, isolated nucleic acids encoding the peptides, and expression. vectors comprising these nucleic acids. The invention includes food additives for preventing oxidation in situ. The invention includes stabilized products with improved storage for products ingredients that are subject to oxidation. Finally, the invention includes methods for isolating peptide fractions having antioxidative activity from protein samples.

17 Claims, 24 Drawing Sheets

Elution Time (min)

Elution Time (min)

ISOLATED ANTIOXIDANT PEPTIDES FORM CASEIN AND METHODS FOR PREPARING, ISOLATING, AND IDENTIFYING ANTIOXIDANT PEPTIDES

FIELD OF THE INVENTION

The present invention relates to antioxidant peptides and methods for isolating antioxidative peptides. More specifically, the present invention relates to antioxidant peptides derived from casein. These antioxidant peptides may be used as food supplements or food additives.

BACKGROUND

Oxidation of oils and fats in foods causes deterioration of flavor and degradation of oil/fat quality. Furthermore, the intake of peroxides produced form lipid oxidation exerts detrimental effects in vivo. Free radicals and active oxygen species generated in the course of oxidation reactions denature proteins in vivo, inactivate enzymes (Szweda et al., "Inactivation of glucose-6-phosphate dehydrogenase, by 4-hydroxy-2-nonene modification of an active-site lysine," *J. Biol. Chem.* 268:3342 (1993)), bring about mutations in DNA (Reiss et al., "DNA-malonaldehyde reaction: Formation of fluorescent products," *Biochem. Biophys. Res. Commun.* 48:921 (1972)), modify low density lipoproteins (Alaiz et al., "Modification of delipidated apoprotein B of low density lipoprotein by lipid oxidation products in relation to macrophage scavenger receptor binding," *Biol. Phar. Bull.* 17:51 (1994)), and contribute to aging and various diseases such as cancer. Dietary antioxidants may help prevent cardiovascular diseases (Krinksy, N. I., "Action of carotenoids in biological systems," *Annu. Rev. Nutri.* 13:561 (1993); Parthasarathy, S., "Mechanisms by which dietary antioxidants may prevent cardioscular diseases," *J. Med. Food* 1:45 (1998)).

Many substances have been identified which have antioxidative activity. These include glutathione, carnosine (Zhou et al., "Ability of carnosine and other skeletal muscle components to quench unsaturated aldehydic lipid oxidation products," *J. Agric. Food Chem.* 47:51(1999)), certain amino acids (Marcuse et al., *Nature*, (1960)), certain proteins, including lactoferrin (Gutteridge et al., *Bioch. J.* 199:259 (1981)), casein (Laakso, "Inhibition of lipid peroxidation by casein. Evidence of molecular encapsulation of 1,4-pentadiene fatty acids," *Biochim. Biophys. Acta* 792:11 (1984)), and certain peptides (Tomita et al., "Antioxidant," U.S. Pat. No. 5,804,555 (1998), Suetsuna et al., "Isolation and characterization of free radical scavenging activities peptides derived from casein," *J. Nurt. Biochem.* 11:128 (2000)). However, because of the importance in preventing oxidation to biological processes and to improved stability of products subject to oxidation, there remains a need to identify new antioxidative compounds, such as antioxidant peptides. Furthermore, there remains a need for a general method that can be used to isolate antioxidative peptides from virtually any protein source.

Miclo et al, U.S. Pat. No. 5,846,939, described a decapeptide from alpha s1 casein with benzodiazepine-type activity which is useful for the treatment of convulsions and anxiety. However, Miclo et al. did not analyze the decapeptide, or fragments thereof, for antioxidative activity.

Shimamura et al., U.S. Pat. No. 5,952,193, described a method for producing a peptide mixture from whey protein utilizing hydrolysis carried out by a protease. In some embodiments, the peptides generated by hydrolysis are further purified. However, Shimamura et al., did not disclose phase separation of the peptides nor determine antioxidative activities of the peptide mixture.

Tomita et al., U.S. Pat. No. 5,804,555, described an antioxidant hydrolysate of lactoferrin. After cleaving lactoferrin with protease, the resulting peptides were purified by reverse phase HPLC. Tomita et al. did not disclose a method for isolating antioxidative peptide fractions that utilizes a separation step that does not result in purified peptide fractions, or that is used in combination with, or in place of, reverse phase HPLC or size-based separation. Additionally, Tomita et al. did not disclose antioxidative peptides of casein, whey, or soy protein. Finally, Tomita et al. did not disclose a phase separation step in isolating antioxidative peptide fragments.

Suestsuna et al. ("Isolation and characterization of free radical scavenging activities peptides [sic] derived from casein," *J. Nutr. Biochem.*, 11:128 (2000)) described peptides with antioxidative activity generated from proteolytic cleavage of casein. Peptides with sequence EL, YFYPEL, FYPEL, YPEL, and PEL were provided. The peptides were purified using a method including several column chromatography-steps.

Thus, there remains a need for additional anti-oxidative peptides and for easier to use, and more cost effective, methods for isolating anti-oxidative peptides. Additionally, there remains a need for a general method of anti-oxidative peptide isolation that can be utilized to isolate peptides from many protein sources.

The current invention provides antioxidative peptides from casein. Furthermore, the current invention includes methods that can be used to isolate antioxidative peptide fractions or antioxidative peptides from any protein source.

SUMMARY OF THE INVENTION

The current invention provides antioxidative peptide fractions. The invention includes antioxidative peptides comprising sequences SEQ ID NOS:1–5. The invention includes methods for making the antioxidative peptides, isolated nucleic acids encoding the antioxidative peptides, and expression vectors comprising these nucleic acids. The invention includes food additives for preventing oxidation in vivo. The invention includes stabilized products with improved storage characteristics which are oxidation resistant. Finally, the invention includes methods for isolating peptide fractions having antioxidative activity from protein samples.

In one aspect, the present invention is an isolated peptide comprising an amino acid sequence selected from the group consisting of SEQ ID NO:1, SEQ ID NO:2, SEQ ID NO:3, SEQ ID NO:4, and SEQ ID NO:5, wherein the peptide has antioxidative activity. In one embodiment, the amino acid sequence is SEQ ID NO:1. In another embodiment, the amino acid sequence is SEQ ID NO:3. In another embodiment, the amino acid sequence is SEQ ID NO:4. In another embodiment, the amino acid sequence is SEQ ID NO:5.

In one aspect, the present invention is an isolated antioxidative casein peptide consisting essentially of an amino acid sequence selected from the group consisting of SEQ ID NO:1, SEQ ID NO:2, SEQ ID NO:3, SEQ ID NO:4, and SEQ ID NO:5. In one embodiment, the antioxidative peptide consists essentially of the amino acid sequence of SEQ ID NO:1. In another embodiment, the antioxidative peptide consists essentially of the amino acid sequence of SEQ ID NO:2. In another embodiment, the antioxidative peptide consists essentially of the amino acid sequence of SEQ ID NO:3. In another embodiment, the antioxidative peptide consists essentially of the amino acid sequence of SEQ ID NO:4. In another embodiment, the antioxidative peptide consists essentially of the amino acid sequence of SEQ ID NO:5.

In another embodiment, the isolated antioxidative casein peptide consists of an amino acid sequence selected from the group consisting of SEQ ID NO:1, SEQ ID NO:2, SEQ ID NO:3, SEQ ID NO:4, and SEQ ID NO:5. In one embodiment, the antioxidative peptide consists of the amino acid sequence of SEQ ID NO:1. In another embodiment, the antioxidative peptide consists of the amino acid sequence of SEQ ID NO:2. In another embodiment, the antioxidative peptide consists of the amino acid sequence of SEQ ID NO:3. In another embodiment, the antioxidative peptide consists of the amino acid sequence of SEQ ID NO:4. In another embodiment, the antioxidative peptide consists of the amino acid sequence of SEQ ID NO:5.

In another aspect, the current invention is a food supplement comprising: an antioxidative peptide comprising an amino acid sequence selected from the group consisting of SEQ ID NQ.1, SEQ IN DO:2, SEQ ID NO:3, SEQ ID NO:4, and SEQ ID NO:5, said antioxidative peptide being present in an amount effective for preventing in vivo oxidation; and an orally-ingestible diluent or carrier. In one embodiment of this aspect of the invention, the amino acid sequence is SEQ ID NO:1. In another embodiment, the amino acid sequence is SEQ ID NO.3. In another embodiment, the amino acid sequence is SEQ ID NO:4. In another embodiment, the amino acid sequence is SEQ ID NO:5.

In another embodiment of this aspect of the invention directed to a food supplement, the antioxidative peptide consists of an amino acid sequence selected from the group consisting of SEQ ID NO:1, SEQ ID NO:2, SEQ ID NO:3, SEQ ID NO:4, and SEQ ID NO:5. In one embodiment, the antioxidative peptide consists of the amino acid sequence of SEQ ID NO:1. In another embodiment, the antioxidative peptide consists of the amino acid sequence of SEQ ID NO:2. In another embodiment, the antioxidative peptide consists of the amino acid sequence of SEQ ID NO:3. In another embodiment, the antioxidative peptide consists of the amino acid sequence of SEQ ID NO:4. In another embodiment, the antioxidative peptide consists of the amino acid sequence of SEQ ID NO:5.

In another aspect, the current invention is a stabilized product comprising: a product ingredient subject to oxidation; and an antioxidative peptide selected from the group consisting essentially of SEQ ID NO:1, SEQ ID NO:2, SEQ ID NO:3, SEQ ID NO:4, and SEQ ID NO:5, wherein the antioxidative peptide is present in an amount effective for preventing oxidation of the product ingredient. In one embodiment of this aspect of the invention directed to a stabilized product, the antioxidative polypeptide consists essentially of the amino acid sequence of SEQ ID NO:1. In another embodiment, the antioxidative peptide consists essentially of the amino acid sequence of SEQ ID NO:2. In another embodiment, the antioxidative peptide consists essentially of the amino acid sequence of SEQ ID NO:3. In another embodiment, the antioxidative peptide consists essentially of the amino acid sequence of SEQ ID NO:4. In another aspect, the antioxidative peptide consists essentially of the amino acid sequence of SEQ ID NO:5.

In another embodiment of this aspect of the invention directed to a stabilized product, the antioxidative peptide consists of an amino acid sequence selected from the group consisting of SEQ ID NO:1, SEQ ID NO:2, SEQ ID NO:3, SEQ ID NO:4, and SEQ ID NO:5. In one embodiment, the antioxidative peptide consists of the amino acid sequence of SEQ ID NO:1. In another embodiment, the antioxidative peptide consists of the amino acid sequence of SEQ ID NO:2. In another embodiment, the antioxidative peptide consists of the amino acid sequence of SEQ ID NO:3. In another embodiment, the antioxidative peptide consists of the amino acid sequence of SEQ ID NO:4. In another embodiment, the antioxidative peptide consists of the amino acid sequence of SEQ ID NO:5.

In one embodiment of this aspect of the invention, the product ingredient subject to oxidation is a food ingredient and the product is a food. In another embodiment, the product ingredient subject to oxidation is a medical diagnostic reagent component and the stabilized product is a medical diagnostic reagent. In another embodiment, the product ingredient subject to oxidation is a pharmaceutical and the stabilized product is a pharmaceutical product.

In another aspect, the current invention is an antioxidative therapeutic compound for treating a disease involving oxidation, wherein the therapeutic compound comprises: an antioxidative peptide comprising an amino acid sequence selected from the group consisting of SEQ ID NO:1, SEQ IN DO:2, SEQ ID NO:3, SEQ ID NO:4, and SEQ ID NO:5, wherein the antioxidative peptide has antioxidative activity, and wherein the antioxidative peptide is present in an amount effective for preventing in vivo oxidation; and a pharmaceutically acceptable carrier. In one embodiment of this aspect of the invention directed to a compound for treating a disease involving oxidation, the antioxidative peptide consists essentially of the amino acid sequence of SEQ ID NO:1. In another embodiment, the antioxidative peptide consists essentially of the amino acid sequence of SEQ ID NO:2. In another embodiment, the antioxidative peptide consists essentially of the amino acid sequence of SEQ ID NO:3. In another embodiment, the antioxidative peptide consists essentially of the amino acid sequence of SEQ ID NO:4. In another embodiment, the antioxidative peptide consists essentially of the amino acid sequence of SEQ ID NO:5.

In another embodiment of this aspect of the invention directed to a therapeutic compound for treating a disease involving oxidation, the antioxidative peptide consists of an amino acid sequence selected from the group consisting of SEQ ID NO:1, SEQ ID NO:2, SEQ ID NO:3, and SEQ ID NO:4. In one embodiment, the antioxidative peptide consists of the amino acid sequence of SEQ ID NO:1. In another embodiment, the antioxidative peptide consists of the amino acid sequence of SEQ ID NO:2. In another embodiment, the antioxidative peptide consists of the amino acid sequence of SEQ ID NO:3. In another embodiment, the antioxidative peptide consists of the amino acid sequence of SEQ ID NO:4. In another embodiment, the antioxidative peptide consists of the amino acid sequence of SEQ ID NO:5.

In another aspect, the current invention provides a method for treating a condition associated with oxidation in a subject, said method comprises administering to the subject an amount of an antioxidative therapeutic compound as described herein. In one embodiment of this aspect of the invention directed to a method for treating a condition associated with oxidation, the subject is a mammal, including a human. In another embodiment of this aspect of the invention directed to a method for treating a condition associated with oxidation, the condition is selected from an inflammatory condition, an allergic condition, and an autoimmune condition. In another embodiment of this aspect of the current invention, the condition associated with oxidation is selected from osteoarthritis, rheumatoid arthritis, ischemia, cataract, corneal pathology, glaucoma, retinal degeneration, vitreal degeneration, cancer, immune deficiency, hyperimmunity, autoimmunity, neurodegeneration, aging, Alzheimer's disease, Huntington's disease, Machoado-Joseph disease, multiple sclerosis, muscular dystrophy, Parkinson's disease, senility, muscular atrophy, stroke, hepatopathies, systemic lupus erythematosus, mixed connective tissue disease, multiple sclerosis, and diabetes.

In another embodiment, the current invention is directed to an isolated nucleic acid encoding an antioxidative peptide, wherein the nucleic acid consists essentially of a nucleotide sequence that encodes the antioxidative peptide having a sequence of the peptide sequences listed as SEQ ID NO:1, SEQ ID NO:2, SEQ ID NO:3, SEQ ID NO:4, and SEQ ID NO:5.

In one embodiment of this aspect of the invention directed to a nucleic acid encoding an antioxidative peptide, the isolated nucleic acid encodes the amino acid sequence of SEQ ID NO:1. In another embodiment, the isolated nucleic acid encodes the amino acid sequence of SEQ ID NO:2. In another embodiment, the isolated nucleic acid encodes the amino acid sequence of SEQ ID NO:3. In another embodiment, the isolated nucleic acid encodes the amino acid sequence of SEQ ID NO:4. In another embodiment, the isolated nucleic acid encodes the amino acid sequence of SEQ ID NO:5.

In one embodiment of this aspect of the invention directed to a nucleic acid encoding an antioxidative peptide, the isolated nucleic acid consists essentially of the nucleotide sequence of SEQ ID NO:6. In another embodiment, the isolated nucleic acid consists essentially of the nucleotide sequence of SEQ ID NO:7. In another embodiment, the isolated nucleic acid consists essentially of the nucleotide sequence of SEQ ID NO:8. In another embodiment, the isolated nucleic acid consists essentially of the nucleotide sequence of SEQ ID NO:9. In another embodiment, the isolated nucleic acid consists essentially of the nucleotide sequence of SEQ ID NO:10.

In one embodiment of this aspect of the invention directed to a nucleic acid encoding an antioxidative peptide, the isolated nucleic acid consists of the nucleotide sequence of SEQ ID NO:6. In another embodiment, the isolated nucleic acid consists of the nucleotide sequence of SEQ ID NO:7. In another embodiment, the isolated nucleic acid consists of the nucleotide sequence of SEQ ID NO:8. In another embodiment, the isolated nucleic acid consists of the nucleotide sequence of SEQ ID NO:9. In another embodiment, the isolated nucleic acid consists essentially of the nucleotide sequence of SEQ ID NO:10.

In another aspect, the current invention provides a recombinant expression vector that expresses an antioxidative peptide, said vector comprising a promoter linked to an antioxidative peptide encoding nucleic acid. The antioxidative peptide encoding nucleic acids useful for this aspect of the invention are those described above.

In another embodiment, the current invention provides a host cell transformed with an antioxidative peptide encoding nucleic acid, as described above. In preferred embodiments, the host cell is transformed with a recombinant expression vector that expresses an antioxidative peptide, as described above.

In another aspect, the current invention provides a method for producing an antioxidative casein peptide in a host cell, said method comprising the steps of:

(a) introducing a nucleic acid encoding an antioxidative peptide having an amino acid sequence selected from SEQ ID NOS:1–5 into a vector, thereby producing an antioxidative casein peptide expression vector;

(b) introducing the antioxidative casein peptide expression vector into the host cell to produce an engineered host cell;

(c) maintaining the engineering host cell under conditions suitable for the expression of an antioxidative casein peptide by the host cell; and (d) collecting the antioxidative casein peptide produced by the host cell.

In preferred embodiments, the host cell is transformed with a recombinant expression vector that expresses an antioxidative peptide, as described above.

In another aspect, the current invention includes methods for identifying antioxidative peptides and fractions containing these peptides. This aspect of the invention includes peptides whose sequence is determined by the methods for identifying antioxidative peptides. The methods of this aspect of the invention utilize a separation step that does not involve column chromatography, to form at least two fractions. In certain embodiments, the separating does not involve substantially purifying any of the peptides.

One embodiment of this aspect of the invention provides a method for identifying an antioxidative peptide from a mixture of peptides, said method comprising:

(a) generating a mixture of peptides suspected of containing an antioxidative peptide or peptides;

(b) separating the peptides in the mixture based on charge or hydrophobicity, using a technique other than column chromatography, to form at least two fractions;

(c) assessing the fractions for antioxidative activity; and (d) treating fractions having antioxidative activity in order to substantially purify the antioxidative peptide or peptides having antioxidative activity.

Another embodiment of this aspect of the invention comprises a method for identifying digested protein fractions containing antioxidative peptides, said method comprising:

(a) digesting a protein with a protease to produce a mixture of peptides;

(b) separating the mixture of peptides by phase separation to produce at least a first phase and a second phase;

(c) assaying the first phase and the second phase for antioxidative activity to determine whether the first phase or the second phase contain antioxidative peptides.

In one preferred embodiment, the method further comprises:

(d) isolating the phases with antioxidative activity; and (e) substantially purifying the antioxidative peptide or peptides in the phases having antioxidative activity.

In another embodiment of this aspect of the invention, the current invention is an antioxidative peptide obtained by the following process:

(a) providing a mixture of peptides suspected of containing an antioxidative peptide or peptides and other macromolecules;

(b) separating the peptides in the mixture based on charge or hydrophobicity, using a technique other than column chromatography, to form at least a first fraction and a second fraction;

(c) assessing the first fraction and the second fraction for antioxidative activity;

(d) isolating the fractions having antioxidative activity; and (e) substantially purifying the antioxidative peptide or peptides in the fractions having antioxidative activity, thereby isolating the antioxidative peptide or peptides.

In certain embodiments, the method further comprises:

(f sequencing the antioxidative peptide or peptides.

In certain embodiments of this aspect of the invention comprising a method involving a separation step, as defined above, or a peptide identified by such a method, the step of separating comprises a step wherein peptides are not substantially purified. In a preferred embodiment, the step of separating comprises a phase separation step.

In certain embodiments of this aspect of the invention, the mixture of peptides are generated by proteolytic cleavage of milk proteins. For certain embodiments of this aspect of the invention, peptide mixtures are generated by proteolytic cleavage of proteins carried out with a protease. In certain embodiments, the protease is selected from the group consisting of glutamyl endopeptidase, corolase PN-L, papain, promod 24 L, validase actinidin, alkaline protease, flavozyme, neutral bacterial proesase Enzyco protease S-11562, Enzyco protease S-11650, Alcalase, and Neutrase. In certain embodiments, the mixture of peptides are generated by proteolytic cleavage of a mixture of proteins such as milk protein, soy protein, and whey protein. In other embodiments, the mixture of peptides are generated by proteolytic cleavage of casein.

In certain preferred embodiments, the phase separation step is carried out by adding acetone to a solution containing the mixture of peptides to form a supernatant and a precipitate. In some embodiments of this aspect of the invention, the step of separating further comprises adding ammonium sulfate to a solution containing the mixture of peptides after the phase separation step, preferably the supernatant, to form an upper layer and a lower layer, wherein the upper layer is the first fraction and the lower layer is the second fraction. In one embodiment, the fraction with antioxidative activity is the first fraction.

DESCRIPTION OF THE PREFERRED EMBODIMENTS

Figure 1:
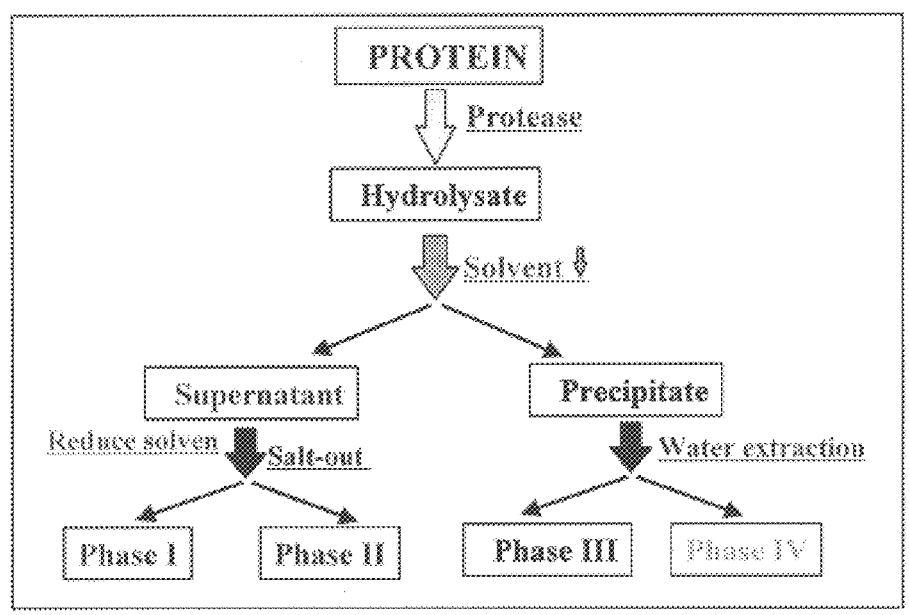
FIG. 1 is a flow diagram of one embodiment of a method for isolating antioxidative peptides of the current invention. The following nomenclature is used: PROTEIN: A protein-containing solution. Protease: Addition of a protease to the protein-containing solution to cleave proteins in the protein-containing solution and form a hydrolysate. Solvent: Addition of organic solvent, for example acetone, to precipitate out from the supernatant unhydrolyzed, intact proteins and/or large polypeptides (Precipitate). Solvent is then reduced from the supernatant by evaporation using a rotary evaporator (Reduce solvent). Ammonium sulfate ($(NH_4)_2SO_4$) is then added, for example, to a final concentration of fifty percent (w/w) (salt-out), and the supernatant is centrifuged Phase I, which contains some acetone, is the upper "oily" phase. Phase II is the lower aqueous phase. Water can be added to extract the acetone precipitate (Water extraction) to obtain a soluble phase (Phase III) and an insoluble phase (Phase IV).

Isolated Peptides. In one aspect, the present invention is an isolated peptide comprising an amino acid sequence selected from the group consisting of SEQ ID NO:1, SEQ ID NO:2, SEQ ID NO:3, SEQ ID NO:4, and SEQ ID NO:5, wherein the peptide has antioxidative activity. In one embodiment, the amino acid sequence is SEQ ID NO:1. In another embodiment, the amino acid sequence is SEQ ID NO:3. In another embodiment, the amino acid sequence is SEQ ID NO:4. In another embodiment, the amino acid sequence is SEQ ID NO:5.

In another aspect, the present invention is an isolated antioxidative casein peptide consisting essentially of an amino acid sequence selected from the group consisting of SEQ ID NO:1, SEQ ID NO0:2, SEQ ID NO:3, SEQ ID NO:4, and SEQ ID NO:5. In certain embodiments the antioxidative peptide consists essentially of an amino acid sequence selected from SEQ ID NOS:1–5.

Additionally, the polypeptides of the invention may contain additional amino acids or other moieties, such as post-translational modifications, that do not inhibit the antioxidative quality of the peptide by more than about 50%, more preferably about 10% The current invention also contemplates non-naturally occurring amino acids (typically those which are not naturally encoded) that do not inhibit the antioxidative quality of the peptide by more than about 50%, more preferably about 10%. Such non-naturally occurring amino acids are well known in the art (see, e.g., Conley et al. "Methods of screening for compounds that interact with human $P_{2u2}$ purinergic receptor," U.S. Pat No. 6,063,582 (2000)). One of ordinary skill can create such modifications, as described herein, using routine synthesis methods and can screen for the effect of such modifications on antioxidation using methods well-known in the art, and as described herein. The peptide may contain from 1–100, more preferably from 1–10, additional amino acids. Some modified versions of the peptides of the current invention are cyclic molecules rather than linear, as illustrated in the Examples section. Illustrations of peptides containing an additional amino acid that does not destroy antioxidative capacity are provided in the Examples section below. For example, the peptide of SEQ ID NO:2 consists essentially of the peptide of SEQ ID NO:1. The peptide of SEQ ID NO:4 consists essentially of the peptide of SEQ ID NO:3.

In another embodiment of this aspect of the invention, the isolated antioxidative casein peptide consists of an amino acid sequence of SEQ ID NOS:1–5.

Casein is the major protein component of non-fat dried milk. Suitable casein for the present invention is mammalian casein, with bovine casein being preferred, and bovine alpha-S1 casein (Genpept accession number AAD14099/GI=1070620) being most preferred. The nucleotide sequence of the bovine casein-coding region is found in Genbank accession number AH007360/GI=1683174.

The term "isolated," as used in this specification, refers to the removal of a chemical or biochemical compound, from its natural environment. The term "isolated," as used in this specification, does not describe any specific level of purity of the antioxidative peptide.

An antioxidative peptide of the present invention has many utilities. For example, the peptide can be used to retard lipid oxidation in products subject to oxidation such as certain food systems, as described in more detail in the "Product Additive" section. The peptide can also be used as a biologically active ingredient for functional foods, as described in more detail in the "Food Additive" section. It can also be used as an active ingredient in pharmaceuticals to prevent and relieve oxidative changes in vivo, as described in the "Therapeutic Compositions" section found herein.

Antioxidative peptides according to SEQ ID NOS:1–5 can be produced in a variety of ways, including methods described in the "Method for identifying antioxidative peptides and peptides identified using the method" section, and illustrated in the Examples section. Furthermore, peptides according to the current invention can be produced by methods involving production and recovery of recombinant proteins and by chemical synthesis, both of which are well known in the art and described in more detail herein. Methods involving production and recovery of recombinant proteins utilize isolated nucleic acids encoding antioxidative peptides, vectors capable of expressing nucleic acids, and recombinant cells in which the vectors capable of expressing antioxidative renox peptides have been inserted, are described herein.

Methods for synthesizing peptides are well-known to skilled workers in the art of immunochemistry, food chemistry, immunology, and/or protein chemistry. For example, but not intended to be limiting, peptides can be synthesized using solid phase F-moc chemistry according to the principles initially described by Merrifield (Merrifield, R. B., "Solid phase peptide synthesis 1. The synthesis of a tetrapeptide," *J. Am. Chem. Soc.* 85:7129 (1963)) with modification subsequently introduced by Meienhofer et al. (Meienhofer, J., et al., "Solid phase synthesis without repetitive acidolysis," J. *Peptide Protein Res.* 13:35 (1979)), and Fields et al. (Fields, C. G., Lloyd, D. H., Macdonald, R. L., Otteson, K. M. & Noble, R. L., "HBTU activation for automated Fmoc solid-phase peptide synthesis," *Peptide Res.* 4:95 (1991)). Typically, such synthesis is carried out on automated peptide synthesizers, such as automated synthesizers available from Applied Biosystems (Foster City, Calif.). An example of a synthesizer that can be used for synthesizing peptides according to the current invention is the Applied Biosystems "Pioneer" system. Once synthesized, sequences are typically verified using an automated peptide sequencer such as a Porton model 2090 (Beckman Instruments Inc., Mountain View, Calif.).

One embodiment of the antioxidative peptides of the present invention is a fusion protein that includes the sequence of SEQ ID NOS:1–5, attached to one or more fusion segments. Suitable fusion segments for use with the present invention include, but are not limited to, a polypeptide that can assist in purification of the peptide to which it is linked. A suitable fusion segment can be a domain of any size that has the desired function (i.e., simplifies purification of the peptides of the invention). Fusion segments can be joined to the amino and/or carboxyl termini of SEQ ID NOS:1–5, and can be susceptible to cleavage in order to enable straight-forward recovery of the antioxidative peptide. Fusion proteins are preferably produced by culturing a recombinant cell transformed with a fusion nucleic acid molecule that encodes a protein including the fusion segment attached to either the carboxyl and/or amino terminal end of the antioxidative peptide of the present invention. Preferred fusion segments include a metal binding domain (e.g., a poly-histidine segment), an immunoglobulin binding domain (e.g., Protein A; Protein G; T cell; B cell; Fc receptor or complement protein antibody-binding domains), a sugar binding domain (e.g., a maltose binding domain), and/or a "tag" domain (e.g., at least a portion of β-galactosidase, a strep tag peptide, a T7 tag peptide, a Flag peptide, or other domains that can be purified using compounds that bind to the domain, such as monoclonal antibodies) More preferred fusion segments include metal binding domains, such as a poly-histidine segment, a maltose binding domain, and a strep tag peptide, such as that available from Biometra (Tampa, Fla.). Fusion proteins can include more than one amino acid sequence of SEQ ID NOS:1–5.

Many assays are known in the art for determining whether a polypeptide has antioxidative activity. A peptide has antioxidative according to the present invention as long as it exhibits antioxidative activity according to at least one assay method. Thus, it is not required to exhibit antioxidative activity in all assays measuring oxidation. Examples of test methods useful for determining antioxidative activity are illustrated in the Examples section and described in more detail in the "Methods for identifying antioxidative peptides and peptides identified using the method" section below.

Food Supplement. In another aspect, the current invention is a food supplement comprising:

an antioxidative peptide comprising an amino acid sequence selected from the group consisting of SEQ ID NOS:1–5, said antioxidative peptide being present in an amount effective for preventing in vivo oxidation; and an orally-ingestible diluent or carrier.

In one embodiment of this aspect of the invention directed to a food supplement, the antioxidative peptide consists essentially of an amino acid sequence selected from the group consisting of SEQ ID NOS:1–5. In another embodiment of this aspect of the invention directed to a food supplement, the isolated antioxidative peptide consists of an amino acid sequence selected from the group consisting of SEQ ID NOS:1–5.

A "food supplement" is an orally ingestible product consumed to improve overall health, well-being, or performance of a subject in an activity and/or an orally ingestible product which provides additional perceived nutritional or biological benefit to a subject.

An "amount effective for preventing in vivo oxidation" can be determined by methods well-known in the art. Effective amounts can be determined by standard techniques for measuring in vivo oxidation. In addition, in vitro assays, such as those described below, may optionally be employed to help identify optimal dosage ranges. Effective doses may be extrapolated from dose-response curves derived from in vitro or animal model test systems. The invention also provides a food supplement pack or kit comprising one or more containers filled with one or more of the food additives of the invention. The amount of the peptide of the current invention to be used as a food supplement can be variable and does not have an upper limit as the peptides themselves are nutrients.

The food supplement of the current invention includes an orally ingestible diluent or carrier. Many orally ingestible diluents or carriers are known in the food sciences. These include, but are not limited to, manufactured cereals, fruit or vegetable products, beverages or beverage concentrates, ground meat products or vegetable analogues thereof, and any inert diluent, carrier, or excipient known in the pharmaceutical art.

Preferably, the antioxidant peptides of the current invention constitute from about 0.0001 to about 10.0% by weight of the food supplement.

The food supplement of the current invention can include additional ingredients. In some embodiments, more than one of the antioxidative casein peptides of the current invention can be included in the same food supplement formulation. Other additional ingredients include any ingestible product. Preferred additional ingredients include, but are not limited to, other active food supplement ingredients such as vitamins and minerals. The food additive may also include acceptable dispersing and suspending agents, and water. Other conventional food supplements can also be included. The food supplement can take many forms including, but not limited to, powders, tablets, capsules, solutions, concentrates, syrups, suspensions, or dispersions.

Product with Improved Stability. In another aspect, the current invention is a stabilized product comprising:

a product ingredient subject to oxidation; and an antioxidative peptide comprising an amino acid sequence selected from the group consisting of SEQ ID NO:1, SEQ IN DO:2, SEQ ID NO:3, SEQ ID NO:4, and SEQ ID NO:5, present in an amount effective for reducing oxidation of the product ingredient subject to oxidation.

"Effective for reducing" means that the reduction in oxidation observed with samples treated with the antioxidative peptides of the current invention is statistically significant when compared to the results using controls (i.e., samples without addition of antioxidative peptides). This statistical significance can be calculated and determined by methods well known in the art. For example, statistical significance can be determined by utilizing a T-test and a 90%, or preferably a 95%, probability cut-off value.

In some embodiments of this aspect of the invention directed to a product additive, the antioxidative peptide consists essentially of an amino acid sequence listed as SEQ ID NOS:1–5. In some embodiments of this aspect of the invention directed to a product additive, the antioxidative peptide consists of one or more amino acid sequences listed as SEQ ID NOS:1–5. In other embodiments of this aspect of the invention directed to a product additive, the antioxidative peptide consists of an amino acid sequence listed as SEQ ID NOS:1–5.

Stabilized products are products that are resistant to oxidative stress that occurs upon product storage over time. This resistance to oxidative stress may result in increased maximum storage time, shelf-life, or expiration dating, or increased consistency of taste and/or other organoleptic properties over time, as compared to products containing the same product ingredient subject to oxidation without the antioxidative peptides of the current invention.

Product ingredients subject to oxidation typically include products that are foods, pharmaceuticals, or medical diagnostics. However, the present invention can include any commercial product ingredient that is subject to oxidation. In one embodiment of this aspect of the invention, the product ingredient subject to oxidation is a food ingredient and the product is a food. In another embodiment, the product ingredient subject to oxidation is a medical diagnostic component and the product is a medical diagnostic. In another embodiment, the product ingredient subject to oxidation is a pharmaceutical and the product is a pharmaceutical product.

Examples of foods that are subject to oxidation include, but are not limited to, frying oils, vegetable oils, corn oil, olive oil, soybean oil, palm oil, safflower oil, olive oil, sunflower oil, cottonseed oil, and the like; fats including natural fats, lards, and synthetic fats, such as are derived from hydrogenated and other edible oils, frying fats, other edible fats, potato flakes, bakery products, meat emulsions, precooked cereals, instant noodles, soybean milk, chicken products, sausage, mayonnaise, salad dressings, margarine, frozen fish, frozen pizza, cheese, pork, beef, fish, fatty meat, cream, butter, sour cream, ice cream or ice milk or other frozen desserts or confections containing milk fat, dried milk, or derivatives thereof.

Typically, the product of the current invention includes a diluent or carrier. Conventional diluents and carriers are known and can be used with the current invention. Any diluent or carrier, including those discussed in other sections herein, can be used with the products of the current invention.

Such stabilized products are different than the food supplements or other aspects of the current invention which are aimed at in vivo oxidation. The stabilized products have reduced oxidation of ingredients subject to oxidation before the products are used. For example, the stabilized product of the current invention have reduced oxidation of product ingredients subject to oxidation before the stabilized products are consumed by or are administered to an organism, such as a human.

Therapeutics and Methods for Treating a Disease Involving Oxidation. The present invention also provides antioxidative therapeutic compound for treating a disease involving oxidation, wherein the therapeutic compound comprises:

an antioxidative peptide with an amino acid sequence consisting essentially of a sequence listed as SEQ ID NOS:1–5, wherein the antioxidative peptide is present in an amount effective for preventing in vivo oxidation; and a pharmaceutically acceptable carrier.

In some embodiments of this aspect of the invention directed to a therapeutic compound, the antioxidative peptide consists essentially of an amino acid sequence listed as SEQ ID NOS:1–5. In some embodiments of this aspect of the invention, the antioxidative peptide consists of more than one amino acid sequence listed as SEQ ID NOS:1–5. In other embodiments of this aspect of the invention, the antioxidative peptide consists of an amino acid sequence listed as SEQ ID NOS:1–5.

In another aspect, the current invention is a method for treating a condition associated with oxidation in a subject, which comprises administering to the subject an effective amount of an antioxidative therapeutic compound as described herein. In one embodiment of this aspect of the invention directed to a method for treating a condition associated with oxidation, the subject is a mammal, and preferably is a human being. Such conditions include an inflammatory condition, an allergic condition, and an autoimmune condition. Other conditions include osteoarthritis, rheumatoid arthritis, ischemia, cataract, corneal pathology, glaucoma, retinal degeneration, vitreal degeneration, cancer, immune deficiency, hyperimmunity, autoimmunity, neurodegeneration, aging, Alzheimer's disease, Huntington's disease, Machoado-Joseph disease, multiple sclerosis, muscular dystrophy, Parkinson's disease, senility, muscular atrophy, stroke, hepatopathies, systemic lupus erythematosus, mixed connective tissue disease, multiple sclerosis, and diabetes.

This aspect of the invention provides for treatment and/or prevention of various diseases and disorders associated with oxidation by administration of an effective amount of an antioxidative therapeutic-compound (termed herein "therapeutic"). Such therapeutics include, but are not limited to, antioxidative peptides of the current invention, food additives of the current invention, stabilized products of the current invention, and nucleic acids encoding antioxidative casein peptides of the current invention.

The invention provides methods of treatment (and prophylaxis) by administration to a subject of an effective amount of a therapeutic of the invention. In a preferred aspect, the therapeutic is substantially purified. The subject is preferably an animal, including, but not limited to, cows, pigs, horses, chickens, cats, dogs, and the like, and more preferably is a mammal, and most preferably is a human.

Various delivery systems are known and can be used to administer a therapeutic of the invention. Such systems include, for example, encapsulation in liposomes, microparticles, microcapsules, recombinant cells capable of expressing the therapeutic (see, e.g., Wu and Wu, "Receptor-mediated in vitro gene transformation by a soluble DNA carrier system," *J. Biol Chem.* 262:4429 (1987)), construction of a therapeutic nucleic acid as part of a retroviral or other vector, and the like. Methods of introduction include, but are not limited to, intradermal, intramuscular, intraperitoneal, intravenous, subcutaneous, intranasal, epidural, and oral routes. The therapeutics may be administered by any convenient route, including, for example, infusion or bolus injection, absorption through epithelial or mucocutaneous linings (e.g., oral mucosa, rectal and intestinal mucosa, and the like) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed (e.g., by an inhaler or nebulizer) using a formulation containing an aerosolizing agent.

In a specific embodiment, it may be desirable to administer the pharmaceutical compositions of the invention locally to the area in need of treatment; this may be achieved by, for example, and not by way of limitation, local infusion during surgery, topical application (e.g., wound dressing), injection, catheter, suppository, or implant (e.g., implants formed from porous, non-porous, or gelatinous materials, including membranes, such as sialastic membranes or fibers), and the like. In one embodiment, administration can be by direct injection at the site (or former site) of a tissue that is subject to damage by oxidation. In another embodiment, the therapeutic can be delivered in a vesicle, in particular a liposome (see Langer, "New methods of drug delivery," *Science* 249:1527 (1990); Treat et al., in *Liposomes in the Therapy of Infectious Disease and Cancer*, Lopez-Berestein and Fidler (eds.), Liss, N.Y., pp. 353–365 (1989)).

In yet another embodiment, the therapeutic can be delivered in a controlled release system. In one embodiment, a pump may be used (see Langer, (1990); Sefton, "Implantable pumps," *Crit. Rev. Biomed. Eng.* 14:201 (1987); Buchwald et al., "Long-term, continuous intravenous heparin administration by an implantable infusion pump in ambulatory patients with recurrent venous thrombosis," *Surgery* 88:507 (1980); and Saudek et al., "A preliminary trial of the programmable implantable medication system for insulin delivery," *N. Engl. J. Med.* 321:574 (1989)). In another embodiment, polymeric materials can be used (see Ranger et al., *Macromol. Sci. Rev. Macromol. Chem.* 23:61 (1983); see also Levy et al., "Inhibition of calcification of bioprosthetic heart valves by local controlled-release diphosphonate," *Science* 228:190 (1985); During et al., "Controlled release of dopamine from a polymeric brain implant: in vivo characterization," *Ann. Neurol.* 25:351 (1989); and Howard et al., "Intracerebral drug delivery in rats with lesion-induced memory deficits," *J. Neurosurg.* 71:105 (1989)). Other controlled release systems discussed in the review by Langer et al. (1990) can also be used.

This aspect of the present invention typically includes a pharmaceutically acceptable carrier. The term "pharmaceutically acceptable" means approved by a regulatory agency of the federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable, or synthetic origin, such as peanut oil, soybean oil, mineral oil, sesame oil, and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The therapeutic, if desired, can also contain minor amounts of wetting or emulsifying agents, or pH buffering agents. These therapeutics can take the form of solutions, suspensions, emulsion, tablets, pills, capsules, powders, sustained-release formulations, and the like. The therapeutic can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, and the like. Examples Aof suitable pharmaceutical carriers are described in "Remington's Pharmaceutical Sciences" by E. W. Martin. Such therapeutics will contain a therapeutically effective amount of the active ingredient, preferably in purified form, together with a suitable amount of carrier so as to provide proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampule of sterile water or saline can be provided so that the ingredients may be mixed prior to administration.

The amount of the therapeutic of the invention which will be effective in the treatment of a particular disorder or condition will depend on the nature of the disorder or condition, as well as the stage of the disorder or condition. Effective amounts can be determined by standard clinical techniques. In addition, in vitro assays, such as those described below, may optionally be employed to help identify optimal dosage ranges. The precise dose to be employed in the formulation will also depend on the route of administration, and should be decided according to the judgment of the health care practitioner and each patient's circumstances. However, suitable dosage ranges for intravenous administration are generally about 20 to about 500 micrograms of active compound per kilogram body weight. Suitable dosage ranges for intranasal administration are generally about 0.01 pg/kg body weight to about 1 mg/kg body weight. Effective doses may be extrapolated from dose-response curves derived from in vitro or animal model test systems. Suppositories generally contain active ingredient in the range of about 0.5% to about 10% by weight; oral formulations preferably contain about 10% to about 95% active ingredient. The invention also provides a pharmaceutical pack or kit comprising one or more containers filled with one or more of the ingredients of the therapeutics of the invention.

In the specific embodiments described above, where the therapeutic is a nucleic acid encoding a protein therapeutic, the nucleic acid can be administered in vivo to promote expression of its encoded protein, by constructing it as part of an appropriate expression vector containing an antioxidative casein peptide as described above in the "Expression vectors" section. Many methods are known for administering a nucleic acid so that it becomes intracellular.

Nucleic acids for use as therapeutics can be tested in suitable animal model systems prior to testing in humans. Such model systems include, but are not limited to, rats, mice, chicken, cows, monkeys, rabbits, and the like.

Isolated Nucleic Acids. In another embodiment, the current invention is directed to an isolated nucleic acid consisting essentially of a nucleotide sequence that encodes a peptide having a sequence of the peptide sequences listed as SEQ ID NO:1, SEQ ID NO:2, SEQ ID NO:3, SEQ ID NO:4, and SEQ ID NO:5.

In certain embodiments of this aspect of the invention directed to a nucleic acid encoding an antioxidative peptide, the isolated nucleic acid encodes a polypeptide consisting essentially of an amino acid sequence selected from SEQ ID NOS:1–5. Such nucleic acids include the nucleic acids encoding a polypeptide with the sequences of SEQ ID NOS:1–5, or slightly altered sequences, wherein at least 50 percent and preferably 90% of the antioxidative activity of the encoded peptide is retained. In other embodiments of this aspect of the invention, the isolated nucleic acid encodes a polypeptide consisting of an amino acid sequence selected from SEQ ID NOS:1–5.

In certain embodiments of this aspect of the invention directed to a nucleic acid encoding an antioxidative peptide, the isolated nucleic acid consists essentially of a nucleotide sequence of SEQ ID NOS:6–10. In other embodiments of this aspect of the invention, the isolated nucleic acid consists of a nucleotide sequence of SEQ ID NOS:6–10.

By "isolated" nucleic acid is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

An isolated nucleic acid encoding an antioxidative peptide of the present invention can be isolated from a natural source or produced using recombinant DNA technology (e.g., polymerase chain reaction (PCR) amplification or cloning) or chemical synthesis. The nucleotide sequence of the antioxidative casein nucleic acids of the current invention can be routinely determined by one of ordinary skill in the art using the genetic code and the peptide sequences of the antioxidative casein peptides of the present invention disclosed in SEQ ID NOS:1–5. The genetic code, which is well-known in the art, is listed in the Table below. For example, the 8 nucleic acid sequences that encode the peptide of SEQ ID NO:5 were determined using the genetic code and are listed as SEQ ID NOS:11–18.

TABLE

The genetic code (DNA)* to amino acids**

| First Position (5' end) | Second position | | | | Third position (3' end) |
|---|---|---|---|---|---|
| | T | C | A | G | |
| T | Phe | Ser | Tyr | Cys | T |
| | Phe | Ser | Tyr | Cys | C |
| | Leu | Ser | Stop (och) | Stop | A |
| | Leu | Ser | Stop (amb) | Trp | G |
| C | Leu | Pro | His | Arg | T |
| | Leu | Pro | His | Arg | C |
| | Leu | Pro | Gln | Arg | A |
| | Leu | Pro | Gln | Arg | G |
| A | Ile | Thr | Asm | Ser | T |
| | Ile | Thr | Asm | Ser | C |
| | Ile | Thr | Lys | Arg | A |
| | Met (start) | Thr | Lys | Arg | G |
| G | Val | Ala | Asp | Gly | T |
| | Val | Ala | Asp | Gly | C |
| | Val | Ala | Glu | Gly | A |
| | Val (Met) | Ala | Glu | Gly | G |

*DNA nucleotide thymidine is indicated. However, as is well known in the art, the protein-synthesizing machinery in a cell utilize RNA to synthesize proteins. In RNA, T residues are uracil residues.
**Stop (och) stands for the ochre termination triplet, and Stop (amb) for the amber, named after the bacterial strains in which they were identified. AUG is the most common initiator codon; GUG usually codes for valine, but, rarely, it can also code for methionine to initiate an mRNA chain.

In one embodiment, the nucleic acids of the current invention are isolated nucleic acids with sequences identical to bovine nucleic acid sequences found in nature that encode for portions of casein. Preferably, the nucleic acid has the sequence selected from the group consisting of SEQ ID NO:6, SEQ ID NO:7, SEQ ID NO:8, SEQ ID NO:9, and SEQ ID NO:10.

Although the phrases "nucleic acid" and "nucleic acid molecule" primarily refer to the physical nucleic acid molecule and the phrase "nucleic acid sequence" primarily refers to the sequence of nucleotides on the nucleic acid molecule, the two phrases can be used interchangeably.

Recombinant Expression Vectors. In another aspect, the current invention is a recombinant expression vector that expresses an antioxidative peptide, comprising a promoter linked to an antioxidative peptide encoding nucleic acid. The antioxidative peptide encoding nucleic acids useful for this aspect of the invention are those described above.

In this embodiment of the present invention, at least one isolated nucleic acid molecule of the present invention is inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid. Recombinant vectors can be used in the cloning, sequencing, producing, and/or otherwise manipulating nucleic acids that encode mammalian peptides of the present invention. One type of recombinant vector, referred to herein as a recombinant molecule, comprises a nucleic acid molecule of the present invention operatively linked to an expression vector. The phrase operatively linked refers to insertion of a nucleic acid molecule into an expression vector in a manner such that the molecule is able to be expressed when transformed into a host cell.

As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, parasite, insect, other animal, and plant cells. Preferred expression vectors of the present invention can direct gene expression in bacterial, yeast, insect, and mammalian cells.

Expression vectors of the present invention contain regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator, and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, insect, or mammalian cells, such as, but not limited to, tac, lac, trp, trc, oxy-pro, omp/lpp, rrnB, bacteriophage lambda (such as lambda pL and lambda pR and fusions that include such promoters), bacteriophage T7, T7lac, bacteriophage T3, bacteriophage SP6, bacteriophage SP01, metallothionein, alpha-mating factor, Pichia alcohol oxidase, alphavirus subgenomic promoter, antibiotic resistance gene, baculovirus, Heliothis zea insect virus, vaccinia virus, herpesvirus, raccoon poxvirus, other poxvirus, adenovirus, cytomegalovirus (such as immediate early promoter), simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with a casein gene, such as bovine or human casein.

Recombinant molecules of the present invention can also contain (a) contain secretory signals (i.e., signal segment nucleic acid sequences) to enable an expressed mammalian peptide of the present invention to be secreted from the cell that produces the peptide and/or (b) fusion sequences which lead to the expression of nucleic acid molecules of the present invention as fusion proteins. Examples of suitable signal segments include any signal segment capable of directing the secretion of a protein of the present invention. Preferred signal segments include, but are not limited to, tissue plasminogen activator (t-PA), interferon, interleukin, growth hormone, histocompatibility, and viral envelope glycoprotein signal segments. Suitable fusion segments encoded by fusion segment nucleic acids are disclosed herein. In addition, a nucleic acid molecule of the present invention can be joined to a fusion segment that directs the encoded protein to the proteosome, such as a ubiquitin fusion segment. Eukaryotic recombinant molecules can also include intervening and/or untranslated sequences surrounding and/or within the nucleic acid sequences of nucleic acid molecules of the present invention.

Transformed Host Cells. In another embodiment, the current invention is a host cell transformed with an antioxidative peptide encoding nucleic acid. In preferred embodiments, the host cell is transformed with a recombinant expression vector that expresses an antioxidative peptide, as described above.

A transformed host cell according to this embodiment of the current invention may be procaryotic or eukaryotic and may be transformed with one or more nucleic acids. A cell can be "transformed," as the term is used in this specification, with a nucleic acid molecule, such as a recombinant expression vector, by any method by which a nucleic acid molecule can be introduced into the cell. Transformation techniques include, but are not limited to, transfection, infection, electroporation, microinjection, lipofection, adsorption, and protoplast fusion. Transformation may be stable or transient. A recombinant cell can remain unicellular or can grow into a tissue, organ, or a multicellular organism. It is to be noted that a cell line refers to any immortalized recombinant cell of the present invention that is not a transgenic animal. Transformed nucleic acid molecules of the present invention can remain extrachromosomal or can integrate into one or more sites within a chromosome of the transformed (i.e., recombinant) cell in such a manner that their ability to be expressed is retained.

Suitable host cells include any cell that can be transformed with a nucleic acid molecule of the present invention. Host cells can be either untransformed cells or cells that are already transformed with at least one nucleic acid molecule (e.g., nucleic acid molecules of the present invention and/or other proteins useful in the production of multivalent vaccines). Host cells of the present invention can be any cell capable of producing at least one peptide of the present invention, and include bacterial, fungal (including yeast), parasite (including helminth, protozoa, and ectoparasite), insect, animal, and plant cells. Preferred host cells include bacterial, mycobacterial, yeast, insect, and mammalian cells. More preferred host cells include Salmonella, Escherichia, Bacillus, Listena, Saccharomyces, Spodoptera, Mycobacteria, Trichoplusia, BHK (baby hamster kidney) cells, MDCK cells (Madin-Darby canine kidney cell line), CRFK cells (Crandell feline kidney cell line), CV-1 cells (African monkey kidney cell line used, for example, to culture raccoon poxvirus), COS (e.g., COS-7) cells, and Vero cells. Particularly preferred host cells are *Escherichia Coli*, including *E. coli* K-12 derivatives; *Salmonella typhi; Salmonella typhimurium*, including attenuated strains such as UK-1 3987 and SR-11 4072; *Spodoptera frugiperda; Trichoplusia ni*; BHK cells; MDCK cells; CRFK cells; CV-1 cells; COS cells; Vero cells; non-tumorigenic mouse myoblast G8 cells (e.g., ATCC CRL 1246), K562 erythroleukemia cells, and mouse NIH/3T3 cells. Additional appropriate mammalian cell hosts include other fibroblast cell lines (e.g., human, murine, or chicken embryo fibroblast cell lines), myeloma cell lines, Chinese hamster ovary cells, LMTK31 cells, and/or HeLa cells. In one embodiment, the peptides can be expressed as heterologous proteins in myeloma cell lines employing immunoglobulin promoters.

A recombinant cell is preferably produced by transforming a host cell with one or more recombinant molecules, each comprising one or more nucleic acid molecules of the present invention operatively linked to an expression vector containing one or more transcription control sequences, examples of which are disclosed herein. A recombinant cell of the present invention includes any cell transformed with at least one of any nucleic acid molecule of the present invention. Suitable and preferred nucleic acid molecules as well as suitable and preferred recombinant molecules with which to transfer cells are disclosed herein.

Recombinant cells of the present invention can also be co-transformed with one or more recombinant molecules including nucleic acid molecules encoding one or more antioxidative peptides of the present invention and one or more other nucleic acid molecules encoding other protective compounds, as disclosed herein (e.g., to produce multivalent vaccines). Recombinant DNA technologies can be used to improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant peptide of the present invention can be improved by fragmenting, modifying, or derivatizing nucleic acid molecules encoding such a protein.

In one embodiment of this aspect of the invention, the transformed host cells are immortalized cell lines capable of expressing high levels of RNA encoding antioxidative peptides of the current invention.

Methods for Producing Peptides of the Current Invention. In another aspect, the current invention is a method for producing an antioxidative peptide in a host cell, said method comprising the steps of:

(a) introducing into a vector a nucleic acid encoding an antioxidative peptide, thereby producing an antioxidative peptide expression vector;

(b) introducing the antioxidative peptide expression vector into the host cell to produce an engineered host cell;

(c) maintaining the engineered host cell under conditions suitable for the expression of an antioxidative peptide by the engineered host cell; and (d) collecting the antioxidative peptide produced by the engineered host cell. In preferred embodiments, the host cell is transformed with a recombinant expression vector that expresses an antioxidative peptide.

For this embodiment, the host cell may be procaryotic or eukaryotic. A preferred cell is a host cell engineered to provide nucleic acids that encode antioxidative peptides, as described above. Effective culture conditions include, but are not limited to, effective media, bioreactor, temperature, pH, and oxygen conditions that permit protein production. An effective medium refers to any medium in which a cell is cultured to produce a antioxidative peptide of the present invention. Such medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH, and oxygen conditions appropriate for a recombinant cell. Such culturing conditions are within the expertise of one of ordinary skill in the art. Depending on the vector and host system used for production, resultant polypeptides of the present invention can remain within the recombinant cell, be secreted into the fermentation medium or into a space between two cellular membranes (e.g., the periplasmic space in *E. coli*), or be retained on the outer surface of a cell or viral membrane.

The phrase "collecting the peptide", as well as similar phrases, refers to collecting the whole medium containing the peptide and need not imply additional steps of separation or purification. Peptides of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing, and differential solubilization. Peptides of the present invention are preferably retrieved in "substantially pure" form. As used herein, "substantially pure" refers to a purity that allows for the effective use of the protein as a therapeutic composition or diagnostic. A therapeutic composition for animals, for example, should exhibit no substantial toxicity and preferably should be capable of stimulating the production of antibodies in a treated animal.

Methods for producing the peptides of the present invention provide peptides for the uses described above, such as, for example, food supplements, product additives, and compounds for treating diseases related to oxidation. Other methods of producing the peptides of the current invention involve direct chemical synthesis, as described above in the "polypeptides" section.

Method for identifying antioxidative peptides and peptides identified using the method. In another aspect, the current invention includes methods for identifying antioxidative peptides and fractions containing these peptides. This aspect of the invention includes peptides whose sequence is determined by the methods for identifying antioxidative peptides. The methods of this aspect of the invention utilize a separation step that separates the peptides based on hydophobicity or charge and use a technique, other than column chromatography, to form at least a first fraction and a second fraction. Typically, this separation step does not involve substantial purification of the peptides, although subsequent separation steps that purify the peptides may be incorporated.

One embodiment of this aspect of the invention is a method for identifying an antioxidative peptide from a mixture of peptides comprising:

(a) generating a mixture of peptides suspected of containing an antioxidative peptide;

(b) separating the peptides based on charge or hydrophobicity, using a technique other than column chromatography, to form at least two fractions;

(c) assessing the fractions for antioxidative activity; and (d) treating the fractions having antioxidative activity in order to substantially purify the antioxidative peptide or peptides having antioxidative activity.

In one embodiment, the method further comprises sequencing the substantially purified antioxidative peptide.

Another embodiment of this aspect of the invention, comprises a method for identifying digested protein fractions containing antioxidative peptides, said method comprising:

(a) digesting a protein with a protease to produce a mixture of peptides;

(b) separating the mixture of peptides by phase separation to produce at least a first phase and a second phase;

(c) assessing the phases for antioxidative activity, thereby identifying the digested protein fractions containing antioxidative peptides.

In one preferred embodiment, the method further comprises:

(d) isolating at least one digested protein fraction with antioxidative activity; and (e) substantially purifying at least one antioxidative peptide from the isolated, digested protein fraction.

In another embodiment of this aspect of the invention, the current invention is an antioxidative peptide obtained by the following process:

(a) providing a mixture of peptides suspected of containing an antioxidative peptide and other macromolecules;

(b) separating the peptides based on charge or hydrophobicity, using a technique other than column chromatography, to form at least a first fraction and a second fraction.

(c) assessing the first fraction and the second fraction for antioxidative activity;

(d) isolating at least one fraction with antioxidative activity; and (e) substantially purifying at least one antioxidative peptide from the isolated fraction with antioxidative activity, thereby isolating at least one antioxidative peptide.

In certain embodiments, the method further comprises:

f) sequencing the antioxidative peptide.

The mixture of peptides can be obtained from many sources. For example, the peptides can be a mixture of peptides synthesized on an automated synthesizer, produced by recombinant DNA techniques, or obtained from proteolytic cleavage of proteins. The proteins include animal proteins (such as those derived from animal milk, eggs, fish, meat, and the like), plant proteins (such as those derived from grains, seaweed, rice, soy, and the like), single-cell proteins (such as those derived from yeasts, bacteria, algae and the like) and mixtures thereof. For example, any food proteins which contain the same amino acid sequences as embodied by the patent may be used as sources of the peptides in the present invention by using appropriate proteases to cleave the peptides from the rest of the protein. Peptide mixtures containing fairly large peptides, for example those with more than 20 amino acids, which are hydrolysates of slightly pre-hydrolyzed proteins and which can be further hydrolyzed by proteases can be used as starting material. In certain preferred embodiments of this aspect of the invention, the mixture of peptides are generated by proteolytic cleavage of soy proteins, whey proteins, or milk proteins. In other aspects, the protein source is a purified protein or mixture of proteins and other components, such as, but not limited to, casein, soy protein and other vegetable/plant proteins.

The starting material for certain embodiments involving protein hydrolysis of this aspect of the invention, are typically aqueous solutions prepared by dissolving the starting protein or slightly pre-hydrolyzed starting protein in water to a concentration of-around 1% to 50%, preferably between around 5% and 25%, most preferably between around 10% and 20%, calculated in terms of protein, and by adjusting the solution pH with an alkali solution or acid solution to a suitable (and preferably optimal) pH for the protease being used.

As discussed above, peptide mixtures used in this aspect of the current invention can be obtained as a result of protein cleavage, for example, by proteases, other enzymes, and/or chemicals. Any protease can be used to generate peptide fragments for embodiments of the current invention involving peptide fragments. Animal-derived (e.g., pancreatin, pepsin, trypsin, and the like), vegetable-derived (e.g., as papain, bromelain, and the like), microbe-derived (e.g., mold, actinomyces, bacteria, lactic acid bacteria, or the like) proteases, or any combination of these, may be selected as desired and added in the prescribed amounts. Other specific proteases useful for the current invention include, but are not limited to, glutamyl endopeptidase (NOVO Nordisk, Bagsvaerd, Denmark), corolase PN-L, papain (e.g., Papain 600, Valley Research Inc., Hammond, Ind.), validase actinidin (Valley Research Inc.), alkaline protease (Valley Research Inc.), neutral bacterial protease (Medipharm AB, Kagerod, Sweden), Enzyco protease S-11562 (Enzyco, Inc., New York, N.Y.), and Enzyco protease S-11650 (Enzyco, Inc.), Enzeco fungal protease concentrate-T (Enzyco, Inc.), Enzeco alkaline protease-L-FG (Enzyco, Inc.), Enzeco bromelain (Enzyco, Inc.), Alcalase (NOVO Nordisk), Neutrase (NOVO Nordisk), Flavozyme (NOVO N.ordisk), and Promod 24 L, Promod 194P, Promod 025P, Promod 278P, Promod 298L (Biocatalysts Ltd., Mid Glamorgan, UK).

In addition to the use of proteases, other means can be used to generate peptide mixtures from proteins for the current invention. For example, chemicals such as cyanogen bromide which cleave peptides at specific sites can be used for the current invention.

In certain preferred embodiments, the mixture of peptides is generated by proteolytic cleavage of-milk proteins, including, for example, casein. In other embodiments, the mixture of peptides is generated by proteolytic cleavage of soy protein. In other embodiments, the mixture of peptides is generated by proteolytic cleavage of whey protein.

The starting material aqueous protein or polypeptide solution to which the prescribed amounts of enzymes have been added is usually maintained for a prescribed time at the optimal temperature of the enzymes to bring about hydrolysis of the protein. When microbial growth is a concern during the hydrolysis, the solution can be maintained as needed for a prescribed time at a temperature higher or lower than the optimal temperature of the enzymes to bring about hydrolysis of the protein. In one preferred embodiment, the starting protein solution is incubated in the presence of the protease for about minutes to about 2 hours at a temperature of about 4° C. to about 60° C., and more preferably for about 60 minutes at about 50° C.

Although not required, it is generally preferred that the enzymes are inactivated or removed in order to stop the hydrolysis. In a preferred embodiment, protease is inactivated at between around about 75° C. and about 85° C. for about 10 minutes.

Many techniques for separating peptides by charge or hydrophobicity, not involving column chromatography, are known in the art and can be used in the above aspects of the invention involving separating steps. Separation techniques useful for the current invention include, but are not limited to, electrophoresis, hydrophobic interaction batch chromatography, chromatofocusing, salting out, phase separation, differential solubilization, and the like.

Many methods for sequencing peptides are known in the art and can be used in this aspect of the current invention. These methods include methods performed using automated protein/peptide sequencers, such as those available from PE Biosystems (Foster City, Calif.). In certain embodiments, these methods utilize Edman degradation. A preferred peptide sequencing technology, for the current invention, as illustrated in the attached Examples, is mass spectrophotography.

One preferred separation technique is phase separation. In a preferred embodiment of using phase separation, the current invention comprises a method for obtaining digested protein fractions containing antioxidative peptides, wherein the method comprises:

(a) digesting a protein with a protease to produce a mixture of peptides;

(b) separating the mixture of peptides by phase separation to produce a supernatant and a precipitate, wherein the supernatant is a digested protein fraction containing antioxidative peptides.

Many methods for phase separation are known in the art and can be used for the current invention. Typically, the phase separation step comprises adding an organic solvent to an aqueous solution containing a mixture of peptides. Many organic solvents are known in the art and can be used with the current invention. In certain preferred embodiments, the phase separation step is carried out by adding acetone to a solution containing the mixture of peptides. Typically for this embodiment, acetone is added to a final concentration of between about 20% and 90%, more typically between about 50% and about 70%.

In some embodiments of this aspect of the invention, the step of separating comprises multiple separation steps which utilize one or more steps and or techniques. In certain embodiments, a phase separation step is followed by a salting out step. For example, the salting out step may be performed by adding ammonium sulfate from 5 to 90% to a solution containing the phase separated mixture of peptides. The total volume of solvent may be reduced prior to ammonium sulfate salting out by evaporation in a rotary evaporator at 40–60° C. In one embodiment, 50% ammonium sulfate is added to the acetone supernatant fraction. Typically, after ammonium sulfate is added, an upper "oily" organic phase and a lower aqueous phase are present. In a preferred embodiment, this aspect of the invention includes the step of collecting the upper "oily" organic phase to obtain a peptide fraction with antioxidative peptides. Examples of methods of separating peptides are illustrated in the Examples section included herein.

"Substantially purifying" as used herein refers to a purity that allows for the effective determination of the amino acid sequence of the peptide. Many methods are known to substantially purify peptides. For example, these methods include sodium dodecyl sulfate polyacrylamide electrophoresis (SDS PAGE), high performance liquid chromatography (HPLC), and capillary electrophoresis (CD). Methods of purifying peptides using reverse phase HPLC are illustrated in the Examples section of this specification.

In one embodiment, reverse phase HPLC is performed on peptide fractions (e.g., the upper "oily" phase) after ammonium sulfate salting out, by first drying the sample with $N_2$ to remove the organic solvent (e.g., acetone). The sample is mixed and centrifuged to remove precipitates before analyzing by reverse phase HPLC. Reverse phase HPLC is performed using a Whatman EQC 5 µl 100A C18 (4.6×250 mm) column (Whatman, Clifton, N.J.), a Hitachi L-6200A pump, an L-4500 diode array detector, and a D6500 DAD HPLC system ((Hitachi Instruments, Inc., San Jose, Calif.).

Two mobile phases (eluents) are used in the HPLC separation for this embodiment; the first mobile phase is 1% acetone containing 0.1% Trifloroacetic acid (TFA), and the second mobile phase is 80% acetone containing 0.05% TFA in double distilled water. The HPLC flow rate is set at a rate of 0.4 ml/min. and ultraviolet absorbance of fractions is measured at 280 nm.

The gradient elution program is set as follows:
  0~26 min, from 80% first mobile phase/20% second mobile phase to 60% first mobile phase/40% second mobile phase
  26~30 min, from 60% first mobile phase/40% second mobile phase to 100% second mobile phase
  30~45 min, with 100% second mobile phase.

In another embodiment especially effective for very hydrophobic peptides, the HPLC flow rate is set at a rate of 0.6 ml/min. and ultraviolet absorbance of fractions is measured at 280 nm.

The gradient program is set as follows:
  0~20 min., from 90% first mobile phase/i 0% second mobile phase to 70% first mobile phase/30% second mobile phase
  20~25 min., from 70% first mobile phase/30% second mobile phase to 50% first mobile phase/50% second mobile phase
  25~26 min., from 50% first mobile phase/50% second mobile phase to 100% second mobile phase
  26~35 min., with 100% second mobile phase.

A preferred method for isolating protein fractions containing antioxidative peptides is shown in FIG. 1. Preferably, Phases I and II are collected as phases containing antioxidative peptides, most preferably Phase I.

Many assays are known for assessing antioxidative activity of a sample. Any of these assays can be used with the current methods. For example, assays can be utilized which measure total antioxidative activity by utilizing 2,2'-azinobis(3-ethylbenzthiazoline-6-sulfonic acid) (ABTS) according to Cox et al., "Biological assays for cellular transformation," *Methods in Enzymology* 238:277 (1994) and Plumb et al., "Are Whole Extracts and Purified Glucosinolates from Cruciferous Vegetables Antioxidants?," *Free Rad. Res.* 25:75 (1996). Other assays can be utilized which measure total reducing power of protein hydrolysate for preformed ABTS radical according to the methods of Pellegrini et al., "Screening of Dietary Carotenoids and Carotenoid-Rich Fruit Extracts for Antioxidant Activities Applying 2,2'-Azinobis(3-ethylenebenzothiazoline-6-sulfonic acid Radical Cation Decolorization Assay," *Methods in Enzymology* 299:379 (1999). This assay measures antioxidant capability as reducing power in terms of scavenging pre-formed ABTS radical.

Another assay that can be used to measure antioxidative activity is an alkyl peroxyl radical quenching assay, (i.e., t-BuOOH-$\beta$-carotene assay) as described in detail in the attached Examples, or as described in publications (Akaike et al., "Determination of Peroxyl Radical-Scavenging Activity in Food by Using Bactericidal Action of Alkyl Peroxyl Radical," *J. Agric. Food Chem.* 43:1864 (1995); Nakao et al., "Alkyl peroxyl radical-scavenging activity of catechins," *Phytochemistry* 49:2379 (1998); Burton et al., "beta-Carotene: an unusual type of lipid antioxidant," *Science* 224:569 (1984)).

Assay methods can be used to measure antioxidant activity of peptide samples in terms of their capability of quenching carbon-centered radicals. In the 2,2'-azobis(2-amidinopropane) dihydrochloride (AAPH) -$\beta$-carotene model system, antioxidant activity of peptide samples is measured in terms of their capability of competing with $\beta$-carotene to quench carbon-centered radicals. In the AAPH-ABTS model system, the peptide's ability to compete with ABTS for quenching carbon-centered radicals is measured. Thus, the relative strength or capacity of the peptide samples to compete with other carbon-center radical quenching agents (e.g., $\beta$-carotene or ABTS) is determined. Further details of the assay used in the Examples section can be found in Tubaro et al., "The Antioxidant Capacity of Complex Mixtures by Kinetic Analysis of Crocin Bleaching Inhibition," *JAOCS* 73:73 (1996); Veliogu, Y. S., et al., "Antioxidant activity and total phenolics in selected fruits, vegetables, and grain products," *J. Agric. Food Chem. JAFC* 46:4113 (1998): and Pryor et al. "A Rapid Screening Test to Determine the Antioxidant Potencies of Natural and Synthetic Antioxidants," *J. Org. Chem.* 58:3521 (1993). Quenching of singlet oxygen can also be used to determine antioxidative capacity. Singlet oxygen assays can be performed according to the methods of Jiang, Z-Y., et al., "Ferrous ion oxidation in the presence of xylenol orange for detection of lipid hydroperoxide in low density lipoprotein," *Analytical Biochem.* 202:384 (1992); Lowum, S. E., et al., "Characterization of dye-sensitized photooxidation of mushroom tyrosinase," *J. Food Biochem.* 13:391 (1989); and Nourooz-Zadeh et al., "Measurement of Hydroperoxides in Edible Oils Using the Ferrous Oxidation in Xylenol Orange Assay," *J. Agdc. Food Chem.* 43:17 (1995), as illustrated in the Examples section below. Another assay method that can be utilized measures the ability of peptide samples (for example, Phase I and II hydrolysate fractions as described in Example 1) to quench superoxide ions or hyxroxyl radicals. The superoxide anion assay can be performed according to the methods of Yen, G. C., et al., "Antioxidant activity of various tea extracts in relation to their antimutagenicity," *J. Agric, Food Chem.* 43:27 (1995): and Nishikimi et al., "The occurrence of superoxide anion in the reaction of reduced phenazine m molecular oxygen," *Biochem. Biophys. Res. Comm.* 46:849 (1972). The hydroxyl radical (Fenton) assay can be performed according to the methods of Lee, B. J., et al., "Antioxidant effects of L-carnosine on liposomes and beef homogenates," *J. Food Sci.* 62:931 (1997).

The following examples describe and illustrate the methods and compositions of the invention. These examples are intended to be merely illustrative of the present invention, and not limiting thereof in either scope or spirit. Unless indicated otherwise, all percentages are by weight. Those skilled in the art will readily understand that variations of the materials, conditions, and processes described in these examples can be used.

EXAMPLE 1

Preparation of Peptide Antioxidants from Milk Proteins

Milk proteins were fractionated by phase separation and ammonium sulfate salting out procedures. Fractions were analyzed for antioxidative activity. The entire process, as shown schematically in FIG. 1, consists of the following steps:

A protein suspension of 20% total solids was prepared by mixing 20 g of non-fat dried milk (NFDM) with 80 g of water. The suspension was brought to 50° C. and proteolysis was begun by adding a protease solution to a final concentration of 1.0% (v/w) separately for each of the proteases shown in Table 1. The sample was then incubated at 50° C. for 60 min. The reaction was then heated to 80° C. for 10 min. to inactivate enzymes. Six volumes of 70% acetone were then added to precipitate out unhydrolyzed, intact proteins and/or large polypeptides. Organic solvent was then reduced by about 50% in the supernatant using a rotary evaporator at 40–60° C. Ammonium sulfate (($NH_4$)$_2SO_4$) was then added to a final concentration of fifty percent, and the supernatant was centrifuged. Phase I, which contained some acetone, was the upper "oily" phase, and Phase II was the lower aqueous phase. Water was then added to extract the acetone precipitate (see above) to obtain a soluble phase, Phase IIl, and an insoluble phase, Phase IV. The concentration of peptides from the prepared protein hydrolysate (Phase I to IV) was then determined.

The concentration of peptides in the sample was determined by the trinitrobenzene sulfonic acid (TNBS) method using Leucine as a standard (Adler-Nissen, "Determination of the degree of hydrolysis of food protein hydrolysates by trinitrobenzenesulfonic acid," *J. Agric. Food Chem.* 27:1256 (1979)). Equal volumes of a sample in about 0.2 M phosphate buffer, pH 8.2, and a 0.1% TNBS solution were combined and incubated at 50° C. for 1 hr. A volume of 0.1 N HCl equal to the total volume of the combined sample and TNBS solution was added to stop the reaction. The sample was then cooled to room temperature. Absorbance at 415 nm was read after 30 min.

Table 1 shows the concentration of peptides in the samples (Phase I) prepared using different proteases. Peptide levels retained in Phase I change due to differences in enzyme specificities, activities, product profiles, and reaction conditions. Only the results of peptide level analysis for Phase I are shown here, because this phase was typically particularly rich in peptide antioxidant activity. Phase II contained relatively low antioxidant activity, whereas Phases IIl and IV had only limited antioxidative activity.

TABLE 1

Concentration of peptides in Phase I prepared from the hydrolysis of different proteases

| Sample:* | A | B | D | E | F | G | I | N | O | P |
|---|---|---|---|---|---|---|---|---|---|---|
| LE (mM) | 21.7 | 36.1 | 43.2 | 38.9 | 20.8 | 48.6 | 43.6 | 42.2 | 48.3 | 40.4 |

*The letters A to P represent different proteases:
A - Glutamyl endopeptidase (SP 446) obtained from *Bacillus licheniformis* (Novo Nordisk);
B - Corolase PN-L;
D - Papain 6000 (Valley Research Inc., Hammond, IN);
E - Promod 24 L (Biocatalysts Ltd., Mid Glamorgan, UK);
F - Validase Actinidin (Valley Research Inc., Hammond, IN);
G - Alkaline protease (Valley Research Inc., Hammond, IN);
I - Flavozyme (Novo Nordisk);
N - Neutral bacterial protease (Medipharm AB, Kagerod, Sweden);
O - Enzyco protease S-11652;
P - Enzyco neutral bacterial protease S-11650.

EXAMPLE 2

Assessment of Antioxidative Activity of Protein Hydrolysate—Total Antioxidant Activity and Total Reducing Power Phase I fractions of the protein hydrolysates generated with various proteases in Example 1 were analyzed for their ability to prevent accumulation of free radicals derived from 2,2'-azino-bis(3-ethylbenzthiazoline-6-sulfonic acid) (ABTS). Both total antioxidative activity and total reducing power of protein hydrolysate using ABTS and preformed ABTS radical, respectively, were used. These two model systems allowed mechanistic information of antioxidative activity of protein hydrolysates to be obtained. Furthermore, the analysis provided specific data related to whether the protein hydrolysates have the capacity of scavenging radicals in an oxidation system.

Total antioxidant assays using ABTS were performed according to Cox et al., "Biological assays for cellular transformation," *Methods in Enzymology* 238:277 (1994); and Plumb et al., "Are Whole Extracts and Purified Glucosinolates from Cruciferous Vegetables Antioxidants?," *Free Rad. Res.* 25:75 (1996). The assay was performed in a total volume of 1.2 ml. Twenty-five microliters of sample (Phase I hydrolysate fractions as described in Example 1 or Trolox standard (2.5 mM) (Aldrich, Milwaukee, Wis.) were combined with 100 µl of ABTS solution (2.5 mM ABTS (Sigma, St. Louis, Mo.) in PBS), 180 µl of MetMb solution (50 µM Metmyoglobin made from mixing 1:1 v/v of 100 M myoglobin (Sigma, St. Louis, Mo.) and 100 µM Metmyoglobin (Sigma, St. Louis, Mo.); and 100 µM potassium ferricyanide (Aldrich, Milwaukee, Wis.) in PBS), and 775 µl PBS. One-hundred and 20 microliters of 10 mM $H_2O_2$ were then added. The mixture was agitated and absorbance was read at 734 nm over a period of 10–15 min.

Total reducing power assays using ABTS radical were performed according to the methods of Pellegrini et al., "Screening of Dietary Carotenoids and Carotenoid-Rich Fruit Extracts for Antioxidant Activities Applying 2,2'-Azinobis(3-ethylenebenzothiazoline-6-sulfonic acid Radical Cation Decolorization Assay," *Methods in Enzymology* 299:379 (1999). This assay measures antioxidant capability as reducing power in terms of scavenging pre-formed ABTS radical. Equal volumes of 10mM PBS and sample (Phase I hydrolysate fractions as described in Example 1) were combined and 2.5 times the total volume (i.e., PBS and sample combined) of a working solution of ABTS radical was added. The mixture was agitated and absorbance at 734 nm was measured after 10 minutes of incubation at 90° C. Acetone or PBS was used as a blank where appropriate. The working solution of ABTS radical was prepared by adding 1 volume of a ABTS radical stock solution to 80 volumes of 10 mM PBS (pH 7.0) and adding, if necessary, PBS or ABTS stock solution to adjust the absorbance to about 0.83 at 734 nm. The ABTS radical stock solution contained 2.5 mM $K_2S_2O_8$ and 6.9 mM ABTS.

Figure 2:
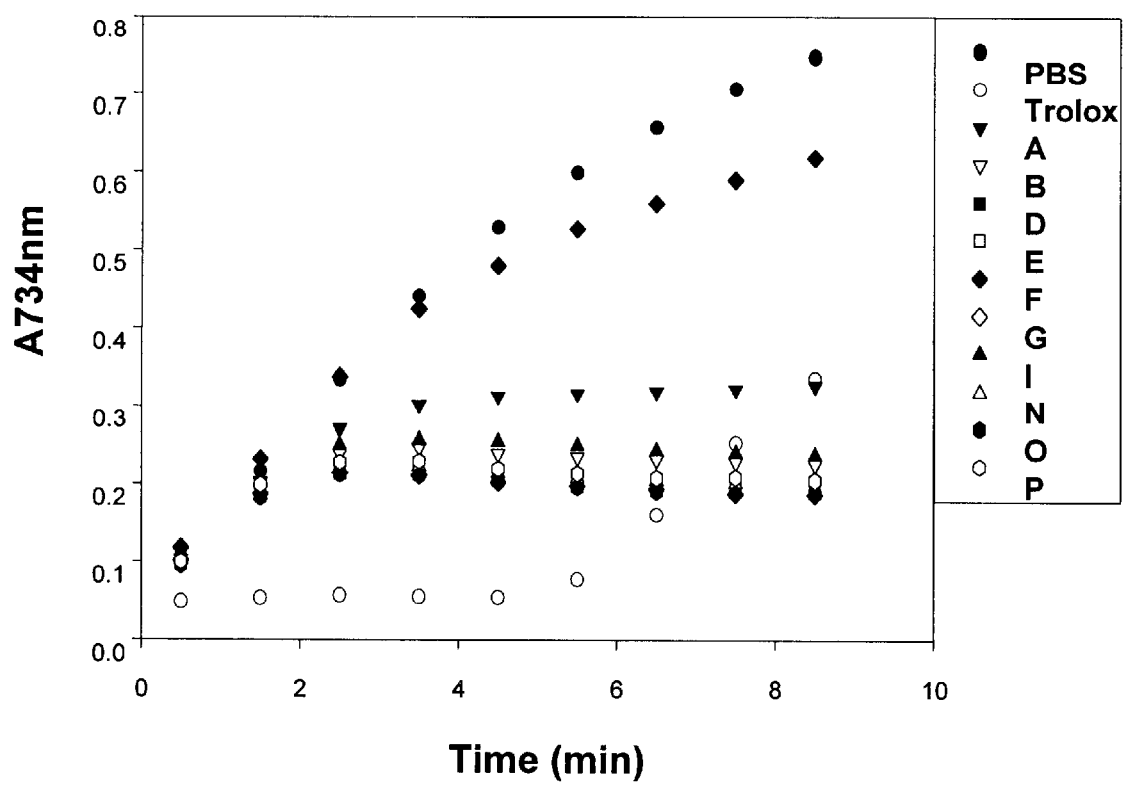
FIG. 2 is a graph of total antioxidant activity of Phase I fractions of milk protein hydrolysate extracts prepared as described in FIG. 1 and Example 1. The letters A to P represent fractions generated by different proteases as described in Table 1. The same volume of protein hydrolysates were added as that of PBS/Trolox controls. The concentration of peptides in the hydrolysate samples are the same as that described in Table 1.

Results of assays measuring total antioxidative activity of the protein hydrolysate are summarized in FIG. 2. Phosphate buffered saline was used as negative control, and the commercial antioxidant Trolox as positive control. Protein hydrolysate produced by protease F (Validase Actinidin, Valley Research Inc., Hammond, Ind.) had a total antioxidative activity similar to the PBS control, indicating that limited levels of peptide antioxidant were produced. All other protein hydrolysates tested show total antioxidative activity in the model system. The progress curve of the commercial antioxidant Trolox shows a typical delay of initiation or lag phase of the oxidation system. In the systems containing protein hydrolysates, however, the progress curves are different from that of Trolox. The results presented in FIG. 2, therefore, suggests different antioxidative mechanisms for protein hydrolysates compared to that of Trolox.

Results of assays measuring the total reducing power of protein hydrolysates produced by different proteases are summarized in Table 2. Leucine was used as a standard for determining the concentration of peptides. PBS was use as negative control. The reducing power of protein hydrolysate is expressed as Trolox equivalent, indicating their relative reducing power per equimolar level of Trolox. As shown in FIG. 2, protein hydrolysate produced by protease F (Validase Actinidin, Valley Research Inc., Hammond, Ind.) had almost no reducing capacity. Protein hydrolysate produced by protease A (Glutamyl endopeptidase, SP 446—obtained from *Bacillus licheniformis*, Novo Nordisk) had about 30% Trolox equivalents. All other protein hydrolysates tested show about 60~70% Trolox equivalents in the model system. These results suggest that radical scavenging capacity could be a primary mechanism of antioxidation of protein hydrolysates.

TABLE 2

Total reducing power of protein hydrolysates against pre-formed ABTS radical

| Sample:* | A | B | D | E | F | G | I | N | O | P |
|---|---|---|---|---|---|---|---|---|---|---|
| Trolox equiv.** | 0.32 | 0.59 | 0.68 | 0.70 | 0.06 | 0.64 | 0.62 | 0.66 | 0.63 | 0.67 |

*The letters A to P represent different proteases as described in Table 1. The same volume of protein hydrolysates were added as that of PBS/Trolox controls. The concentration of peptides in the hydrolysate samples are the same as that described in Table 1.
**Total antioxidant activity (reducing power in terms of scavenging pre-formed ABTS radical) is expressed as Trolox equivalents (defined as the relative reducing power of the peptide sample compared to an equimolar level of Trolox).

EXAMPLE 3

Assessment of Antioxidative Activity of Protein Hydrolysate—Quenching of Alkyl Peroxyl Radicals An analysis was performed to determine the antioxidative activity of the Phase I fractions of protein hydrolysates generated with various proteases in Example 1 by measuring the quenching of alkyl peroxyl radicals. A t-butoxy peroxide/β-carotene assay was used based on several published assays ((Akaike et al., "Determination of Peroxyl Radical-Scavenging Activity in Food by Using Bactericidal Action of Alkyl Peroxyl Radical ," *J. Agric. Food Chem.* 43:1864 (1995); Nakao et al., "Alkyl peroxyl radical-scavenging activity of catechins," *Phytochemistry* 49:2379 (1998); Burton et al., "beta-Carotene: an unusual type of lipid antioxidant," *Science* 224:569 (1984)). The assay involves the following two sequential reactions:

i) t-BuOOH+MetMb→t-BuOO. (1)

ii) t-BuOO.+β-carotene→bleaching (2)

The reaction of the peroxyl radical with βcarotene results in the disappearance of yellow color associated with β-carotene (i.e., bleaching). Absorbance measured at 452 nm indicates that antioxidants effectively compete for peroxyl radical and prevent bleaching. Results from this test indicate the relative alkyl peroxyl radical quenching capacity of protein hydrolysates compared to β-carotene.

For this assay, 725 μl of 10 mM PBS was combined with 120 μl of Tween 20 (2.4%) and 120 μl of MetMb (50 μM MetMb made from mixing 1:1 v/v of 100 μM myoglobin (Sigma, St. Louis, Mo.) and 100 μM potassium ferricyanide (Aldrich, Milwaukee, WI) in PBS), and the mixture was incubated at 37° C. β-carotene (saturated solution in acetone at 37° C.) was then added, and the solution was mixed. Then 25 μl of sample (Phase I hydrolysate fractions as described in Example 1 or Trolox standard (0.5 to 10 mM)) and 150 μl of 50 mM t-BuOOH in PBS was added. The sample was mixed, and absorbance read at 452 nm at 30 s and then 1 minute intervals for about 12 or 15 minutes. PBS or acetone was used as a blank where appropriate.

Figure 3:
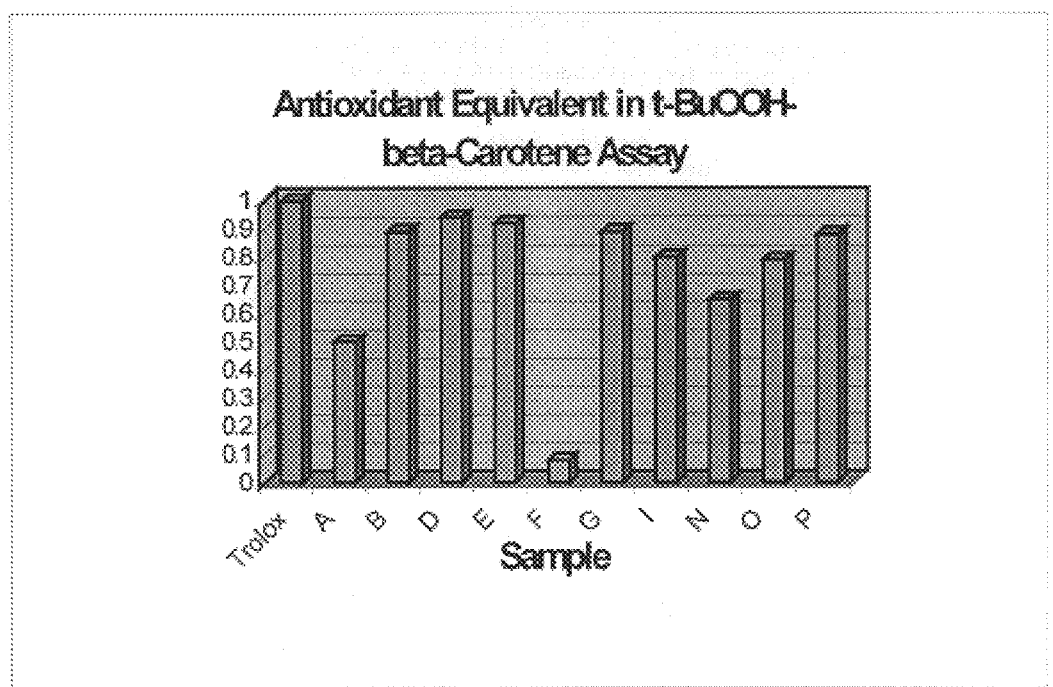
FIG. 3 is a graph of antioxidant equivalent in the t-BuOOH-beta-carotene assay of Phase I fractions of hydrolysate extracts prepared as described in FIG. 1 and Example 1. The letters A to P represent fractions generated by different proteases as described in Table 1. The same volume of protein hydrolysates were added as that of PBS/Trolox controls. Alkyl peroxyl radical quenching capacity is expressed as Trolox equivalents (defined as the relative quenching capacity of the peptide sample compared to an equimolar level of Trolox).

FIG. 3 shows the relative alkyl peroxyl radical quenching capacity of protein hydrolysates produced by different proteases. PBS was used as negative control. Trolox equivalents were expressed based on an integration of absorbance over time within a 15 minute assay period. Similar to those shown in FIG. 2, protein hydrolysate produced by protease F (Validase Actinidin, Valley Research Inc., Hammond, Ind.) had almost no antioxidative activity. Protein hydrolysate produced by protease A (Glutamyl endopeptidase, SP 446: obtained from Bacillus licheniformis, Novo Nordisk) had about half of Trolox equivalents of that produced by protease D. Protein hydrolysates produced by protease B, D, E, G, and P all had above 80% Trolox equivalents, indicating their effectiveness of quenching alkyl peroxyl radical in the model system.

EXAMPLE 4

Assessment of Antioxidative Activity of Protein Hydrolysate—Quenching of Carbon-centered Radicals (using 2,2'-azobis(2-amidinopropane) dihydrochloride, AAPH)

An analysis was performed to determine the antioxidative activity of the Phase I fractions of protein hydrolysates generated with various proteases in Example 1 by measuring the quenching of carbon-centered radicals. Two assay methods were developed for determining antioxidant activity of peptide samples in terms of their capability of quenching carbon-centered radicals. In the 2,2'-azobis(2-amidinopropane) dihydrochloride (AAPH)—β-carotene model system (derived from Tubaro et al., "The Antioxidant Capacity of Complex Mixtures by Kinetic Analysis of Crocin Bleaching Inhibition," *JAOCS* 73:173 (1996); Veliogu, Y.S., et al., "Antioxidant activity and total phenolics in selected fruits, vegetables, and grain products," *J. Agric. Food Chem.* 46:4113; and Pryor et al., "A Rapid Screening Test to Determine the Antioxidant Potencies of Natural and Synthetic Antioxidants," *J. Org. Chem.* 58:3521 (1993)), antioxidant activity of peptide samples is measured in terms of their capability of competing with β-carotene to quench carbon-centered radicals. In the AAPH-ABTS model system, the peptide's ability to compete with ABTS to quench carbon-centered radicals is measured. Results of the experiments indicate the relative strength or capacity of the peptide samples to compete with other carbon-center radical quenching agents (e.g., β-carotene or ABTS). The results of these experiments provide information about the antioxidative mechanism of the peptide antioxidants of the present invention.

For the AAPH-β-carotene assay described above, 910 μl of 10 mM PBS and 120 μl of 2.4% Tween 20 were combined and incubated at 50° C. Sixty microliters of a β-carotene acetone solution (saturated solution containing 0.3% linoleic acid) was added followed by 25 μl of the sample (i.e., Phase I hydrolysate fractions as described in Example 1) and 25 μl of 500 mM AAPH (freshly prepared in PBS). The mixture was agitated and absorbance read at 452 nm at 50° C. for 10–15 minutes.

For the AAPH-ABTS assay described above, 1050 μl of 10 mM PBS were added to 100 μl of a 2.5 mM ABTS solution and incubated at 50° C. for at least 5 min. Twenty-five microliters of the sample (i.e., Phase I hydrolysate fractions as described in Example 1) were then added, followed by 25 μl 500 mM AAPH. The mixture was agitated and absorbance read at 734 nm at 50° C for 10–15 minutes.

Figure 4:
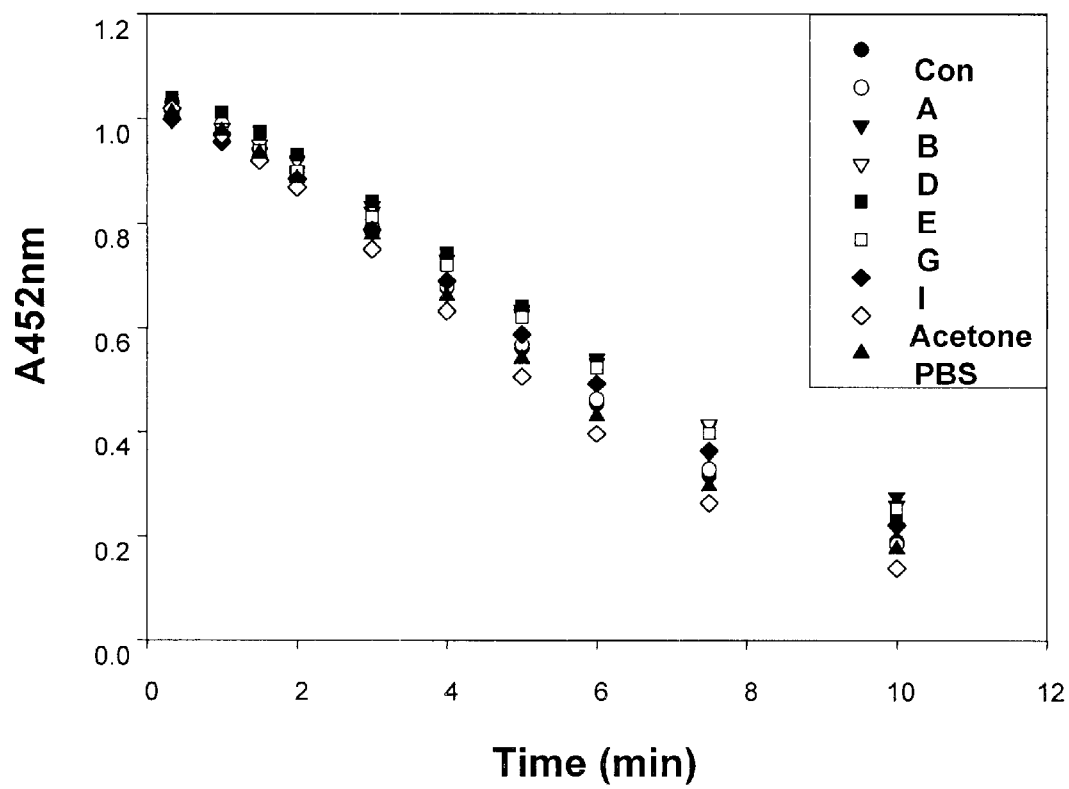
FIG. 4 is a graph of AAPH-β-carotene assay results for Phase I fractions of hydrolysate extracts prepared as described in FIG. 1 and Example 1. The letters A, B, D, E, G, and I represent different proteases as described in Table 1. The same volume of protein hydrolysates were added as that of PBS/acetone controls.

Results of the AAPH-β-carotene assay, shown in FIG. 4, indicate that the peptide samples could not effectively compete with β-carotene to quench carbon-centered radicals. As β-carotene is an excellent radical quenching agent, the results presented here are not unexpected.

Figure 5:
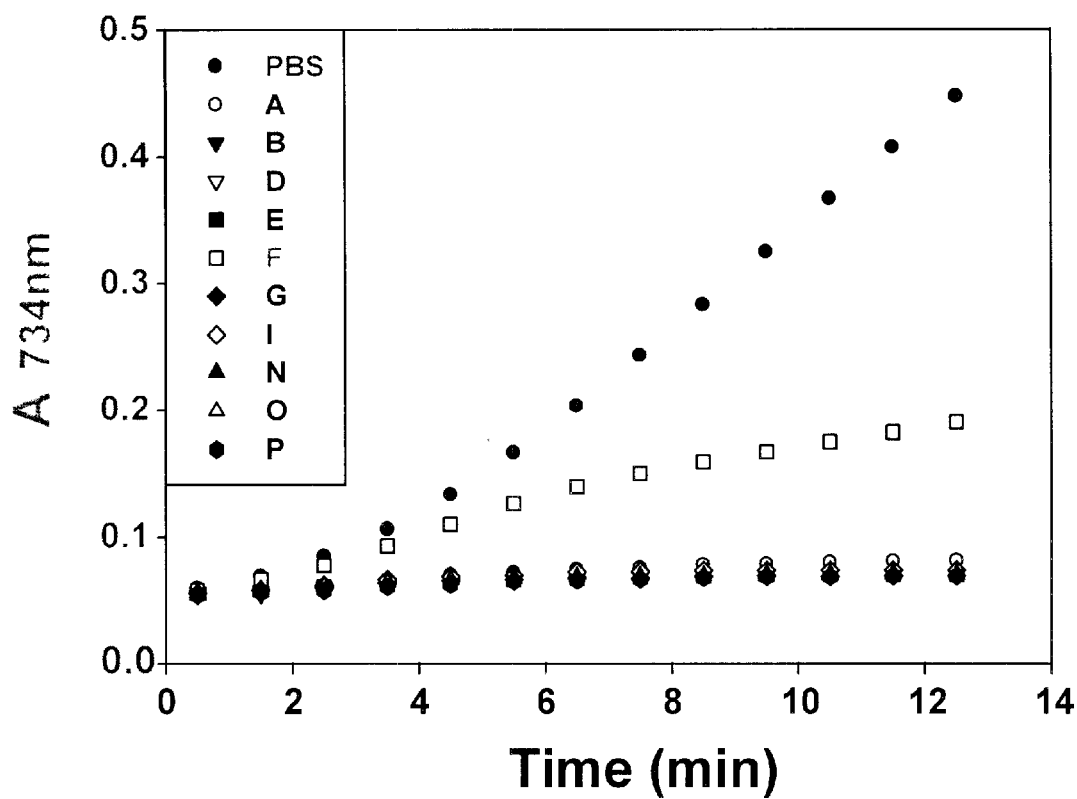
FIG. 5 is a graph of results of AAPH-ABTS assay of Phase I fractions of hydrolysate extracts prepared as described in FIG. 1 and Example 1. The letters A to P represent different proteases as described in Table 1. The same volume of protein hydrolysates were added as that of PBS controls. Low absorbance at 734 nm over time indicates a stable system due to the presence of antioxidants.

In contrast with the results of the AAPH-β-carotene assay, shown in FIG. 4, most of the peptide samples prepared (except the sample produced by protease A) effectively competed with ABTS to quench carbon-centered radicals in the AAPH-ABTS assay (see FIG. 5). While some of this antioxidant effect may be attributable to general reducing power of the peptide samples (as indicated in FIG. 2 and Table 2), it is evident by the magnitude of quenching observed that the effect observed in the AAPH-ABTS assay was greater than could be accounted for on the basis of reducing power alone.

EXAMPLE 5

Assessment of Antioxidative Activity of Protein Hydrolysate—Quenching of Singlet Oxygen An analysis was performed to determine the antioxidative activity of Phase I fractions of protein hydrolysates generated with various proteases in Example 1 by measuring the quenching of singlet oxygen. This assay method was used to evaluate the ability of the peptide samples (Phase I hydrolysate fractions as described in Example 1) to quench singlet oxygen. Singlet oxygen ($^1O_2$) is very electrophilic and reacts with C=C bonds. The lifetime of singlet oxygen in water is markedly less than in non-polar or lipid phase. The longer half-life of singlet oxygen in the lipid phase favors oxidation of lipids. Therefore, $^1O_2$ is considered as a main component responsible for the initiation of lipid oxidation.

The singlet oxygen assay was performed according to the methods of Jiang, Z-Y., et al., "Ferrous ion oxidation in the presence of xylenol orange for detection of lipid hydroperoxide in low density lipoprotein," *Analytical Biochem.* 202:384 (1992) and Lowum, S. E., et al., "Characterization of dye-sensitized photooxidation of mushroom tyrosinase," *J. Food Biochem.* 13:391.M (1989). For the assay, 955 μl 10 mM PBS, 75 μl sample (Phase I hydrolysate fractions as described in Example 1), and 120 μl linoleic acid-Tween 20 (0.3% linoleic acid v/v, 1.2% Tween 20 v/v in PBS) were combined. To this solution, 100 μl of rose Bengal (20 mg/10 ml PBS) was added, the solution was mixed, placed under a light source (60 w incandescent, 3.5 cm distance from light source to sample tube), and incubated at 24–25° C. At specific time points, 100 μl of reaction solution was combined with 0.9 ml FOX reagent and absorbance was read at 560 nm after 30 min. of incubation. FOX reagent was prepared by combining 900 ml MeOH, 100 ml 250 mM $H_2SO_4$, 880 mg BHT, 76 mg xylenol orange and 98 mg ammonium ferrous sulfate hexahydrate. Acetone or PBS was used as blank, where appropriate.

Figure 6:
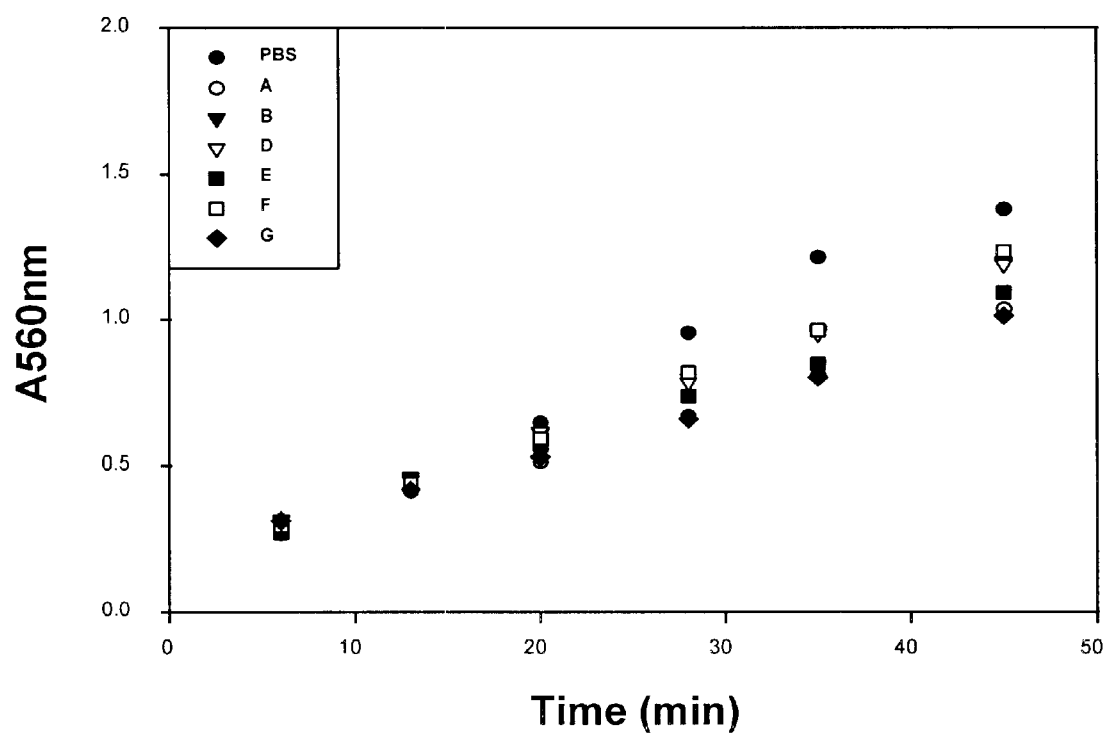
FIG. 6 is a graph of singlet-oxygen assay results of Phase I fractions of hydrolysate extracts prepared as described in FIG. 1 and Example 1. The letters A, B, D, E, F, G, I, N, O, and P represent different proteases used for preparing protein hydrolysates as described in Table 1.

FIG. 6 shows the capacity of quenching singlet oxygen of the peptide samples in the model test system. The peptide samples showed the capacity to quench singlet oxygen in the model system. Like previous experiments, peptide samples prepared by protease F shows the least quenching capacity compared to other peptide samples.

The antioxidative activity determinations in this system are minimum estimates because the accumulation of peroxides presumably from both linoleic acid and peptides, is being measured. Since peptides may form peroxides during the course of acting as antioxidants in this assay, peptide-derived peroxides will contribute to the pool of peroxides being measured, even though linoleic acid is being protected. Thus, the antioxidant activity of the peptides may be greater than reported in this assay.

EXAMPLE 6

Assessment of Antioxidative Activity of Protein Hydrolysate—Quenching of Superoxide Anion An analysis was performed to evaluate the ability of the peptide samples (Phase I and II hydrolysate fractions as described in Example 1) to quench the superoxide ion. Superoxide anion generated in a lipid system acts as a nucleophilic reagent. It is not a strong oxidizing agent and is not able to abstract an H-atom to initiate lipid peroxidation. In acidic environments, the protonated superoxide anion becomes a perhydroxyl radical that can directly abstract an H-atom to initiate lipid peroxidation.

The superoxide ion assay was performed according to the methods of Yen, G. C., et al., "Antioxidant activity of various tea extracts in relation to their antimutagenicity," *J. Agric, Food Chem.* 43:27 (1995); Nishikimi et al., "The occurrence of superoxide anion in the reaction of reduced phenazine m molecular oxygen," *Biochem. Biophys. Res. Comm.* 46:849 (1972). For this assay, 120 μl 15 mM phenazine methosulfate (PMS) in 0.1 M phosphate buffer, pH 7.4, 120 μl 37.5 mM nitro blue tetrazolium (NBT) in phosphate buffer, 735 μl phosphate buffer (0.1 M, pH 7.4), and 25 μl sample (Phase I and II hydrolysate fractions as described in Example 1) were combined. To this solution, 200 μl 117 mM NADH solution was added, to start the reaction. The solution was agitated and absorbance read at 560 nm after 5 minutes. PBS was used as a control.

Figure 7:
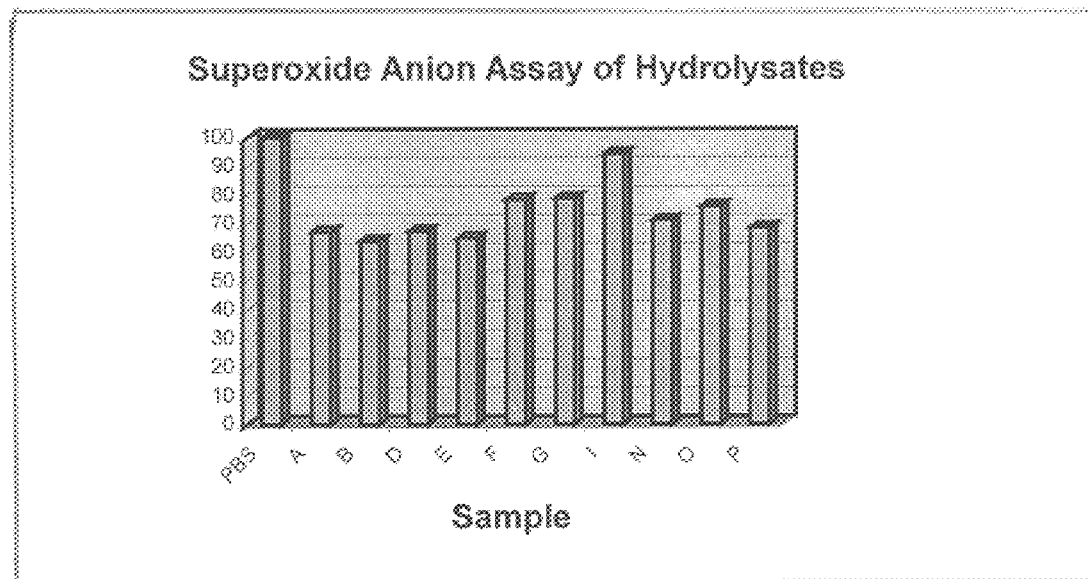
FIG. 7 is a series of bar graphs showing superoxide anion assay of Phase I fractions of hydrolysate extracts prepared as described in FIG. 1 and Example 1. The letters A to P represent different proteases used for preparing protein hydrolysates as described in Table 1. The same volume of protein hydrolysates were added as that of PBS controls in the assay.

FIG. 7 shows the capacity of the hydrolysate fractions to quench superoxide anion in a model system. The PBS control showed no quenching capacity and the levels of superoxide generated in the sample was assigned a value of 100. The reduced absorbance value obtained with a sample, compared to the value obtained for the control in FIG. 7 represent the relative levels of superoxide trapped by the reporter compound NBT. Because acetone interfered in this assay, the peptide samples used for the experiments were a mixture of Phase I and II after the removal of solvent; this is different from Examples 2–5 when only Phase I fractions were used.

The peptide samples showed different levels of capacity of quenching superoxide anion in the model system. Peptide samples B and E were most antioxidative in this system, affording about 40% inhibition. Unlike the results obtained previously, peptide sample produced by protease F had better superoxide anion quenching capacity (>20%) than that produced by protease I (~5% inhibition). These results suggest that peptides present in Phase II of the protease F sample, contain antioxidative activity and may react by a different mechanism.

EXAMPLE 7

Assessment of Antioxidative Activity of Protein Hydrolysate—Quenching of Hydroxyl Rradical An analysis was performed to evaluate the ability of the peptide samples (Phase I and II hydrolysate fractions as described in Example 1) to quench the hydroxyl radical. The hydroxyl radical is an exceptionally active agent that reacts nonselectively with all organic constituents of food. Consequently, it can directly initiate lipid oxidation in food systems. The capacity to quench hydroxyl radicals, therefore, should theoretically be a very important characteristics for food antioxidants.

The hydroxyl radical (Fenton) assay was performed according to the methods of Lee, B. J., et al., "Antioxidant effects of L-carnosine on liposomes and beef homogenates," *J. Food Sci.* 62:931 (1997). For this assay, 945 μl buffer (0.1 M phosphate buffer, pH 7.4), 60 μl EDTA-$FeCl_3$ solution (92 mM EDTA, 26 mM $FeCl_3$ in 0.1 M phosphate buffer pH 7.4), 25 μl sample (Phase I and II hydrolysate fractions as described in Example 1 or Trolox standard (2.5 mM)), and 120 μl of 1 mM H₂O₂ were combined. To this solution, 50 μl of a deoxyribose-ascorbic acid solution (67 mM deoxyribose, 4.8 mM ascorbic acid, in 01 M phosphate buffer pH 7.4) was added, and the solution was mixed and incubateded at 37° C. for 1 hr. An aliquot of this solution was combined with an equal volume of a TCA (trichloroacetic acid)/TBA (2-thiobarbituric acid) solution (prepared by dissolving 15 g TCA, and 0.375 g TBA in 0.25N HCl to a final volume of 100ml, and adding 2 ml 0.2% butylated hydroxyatoluene (BHT) in ethanol solution immediately before use). The resulting sample/TCA/TBA solution was mixed and boiled for 10 min. Absorbance of the solution is then read at 532 nm after cooling to room temperature. PBS was used as a control.

Figure 8:
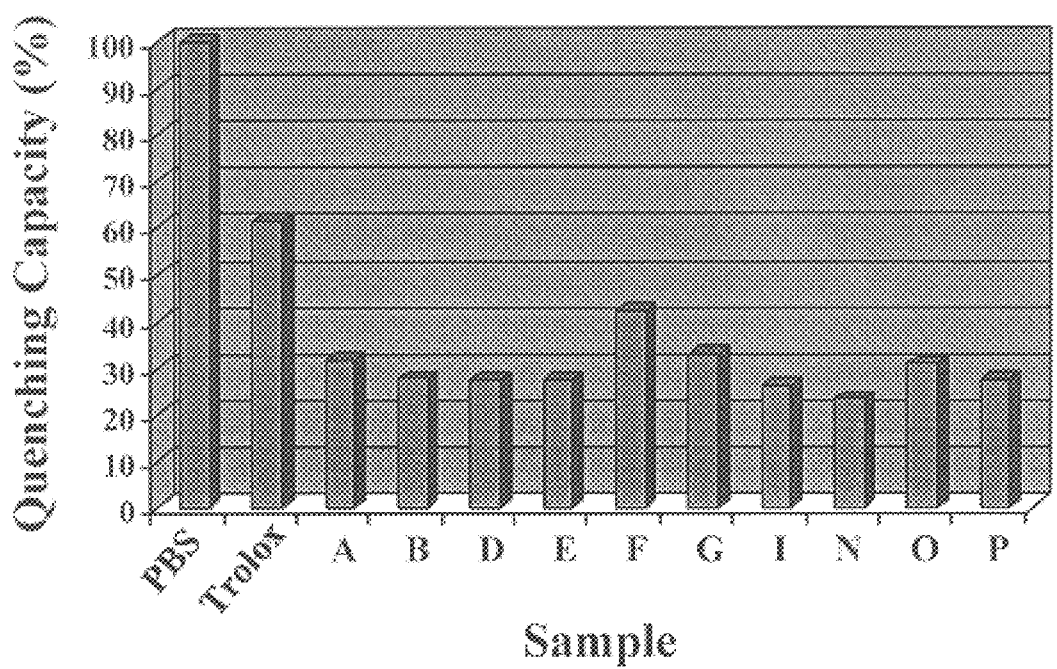
FIG. 8 is a series of bar graphs illustrating the results of superoxide anion assay of Phase I fractions of hydrolysate extracts. The letters A to P represent different proteases used for preparing protein hydrolysates as described in Table 1. PBS and Trolox were used as negative and positive antioxidant controls, respectively. The same volume of protein hydrolysates were added as that of controls in the assay.

FIG. 8 shows results of the assays measuring the capacity of the peptide samples to quench hydroxyl radicals in the model system. The PBS control showing no quenching capacity was assigned a value of 100. Lower values in this figure represent the degree of trapping of hydroxyl radical. Because acetone interfered in this assay, the peptide samples used for the experiments were a mixture of Phase I and II after the removal of solvent.

Results shown in FIG. 8 indicate that all protein hydrolysates prepared possess the capacity to quench hydroxyl radicals in a model system. The peptide samples showed different levels of hydroxyl radical quenching in the model system. Although the peptide sample produced by protease F also showed the lowest hydroxyl radical quenching capacity of peptide samples, at the level added, its quenching capacity is better than Trolox. These results suggest that peptides present in Phase II of the protease F sample, contain antioxidative activity and may react by a different mechanism.

EXAMPLE 8

Antioxidative Activity of HPLC Isolated Peptides from the Phase I Fraction of Milk Proteins Cleaved with Glutamyl Endopeptidease from *Bacillus licheniformis*

An analysis was performed of antioxidative activity of hydrolysate fractions generated after digestion of milk proteins with glutamyl endopeptidase from *Bacillus licheniformis* (protease A from Examples 1–7).

Phase I fractions from protein hydrolysates with glutamyl endopeptidase from *Bacillus licheniformis* as described in Example 1 were prepared for HPLC analysis by drying the sample collected from Phase I (see FIG. 1) with N₂ to remove acetone. The dried sample was dissolved in 1:1 (v/v) dH2O:eluent A (HPLC first mobile phase described below). The sample was mixed and centrifuged to remove precipitates before analyzing by reverse phase HPLC. Reverse phase HPLC was performed using a Whatman EQC 5 μl 100A C18 (4.6×250 mm) column (Whatman, Clifton, N.J.), a Hitachi L-6200A pump, an L-4500 diode array detector, and a D6500 DAD HPLC system.

Two mobile phases (eluents) were used in the HPLC separation; the first mobile phase was 1% acetone containing 0.1% Trifluoroacetic acid (TFA) in dH₂O, and the second mobile phase was 80% acetone containing 0.05% TFA in dH₂O. The HPLC flow rate was set at a rate of 0.4 ml/min. and ultraviolet absorbance of fractions was measured at 280 nm.

The gradient elution program was set as follows:

0–26 min., from 80% first mobile phase/20% second mobile phase to 60% first mobile phase/40% second mobile phase 26–30 min., from 60% first mobile phase/40% second mobile phase to 100% second mobile phase 30–45 min., with 100% second mobile phase.

Antioxidative activity of the fractionated 280 nm absorbance peaks from HPLC was measured using the ABTS radical assay as described in Example 2 above.

Figure 9:
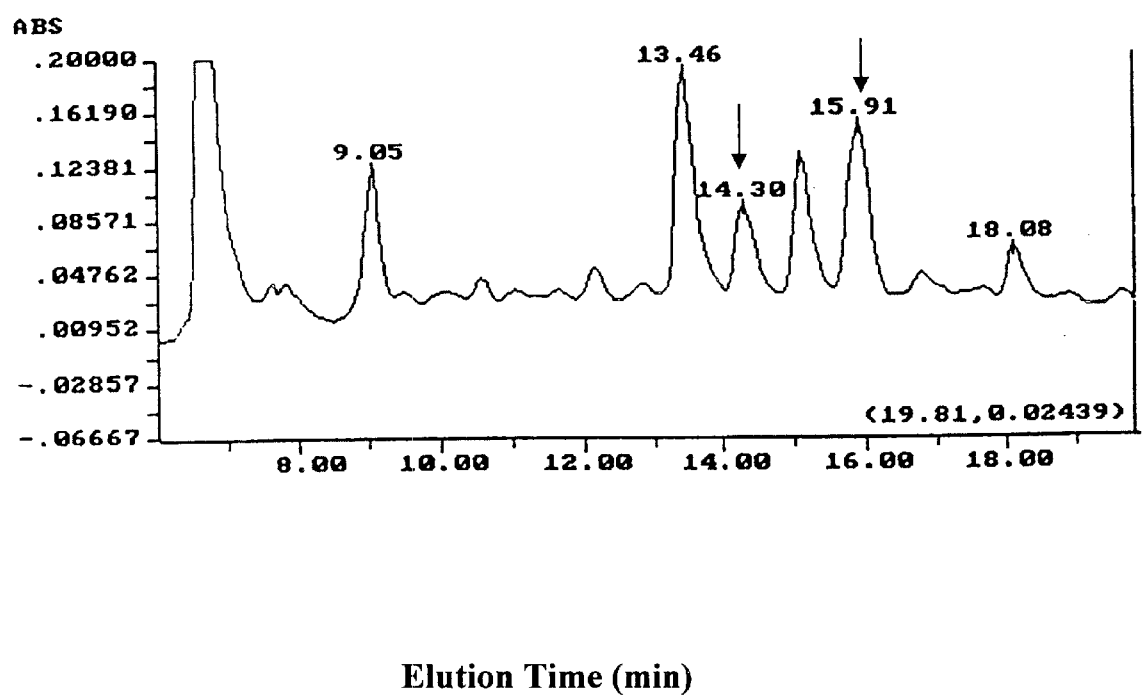
FIG. 9 is an HPLC chromatograph of peptides separated from Phase I fractions generated according to the method for isolating antioxidative peptides shown schematically in FIG. 1 and described in detail in Example 1. Glutamyl endopeptidease of *Bacillus licheniformis* was used as the protease. Peptides of fraction of elution time 13.46 and 18.08 minutes are discussed in Examples 8 through 10. Peptides of fractions of elution time 14.30 and 15.91 minutes are discussed in Examples 11 through 13.

FIG. 9 shows the HPLC chromatograph of protein hydrolysates obtained from Phase I (see Example 1). Several peptides were included in the phase. The main peak at 13.46 min. elution time was collected for further analysis. In addition, a fraction at 18.08 min. elution time was collected. Further analysis revealed that the 18.08 min. peptide had the same sequence as the 13.46 minute peptide except that it was one amino acid longer. (see Example 9.) These two fractions, therefore, were analyzed side by side.

Figure 10:
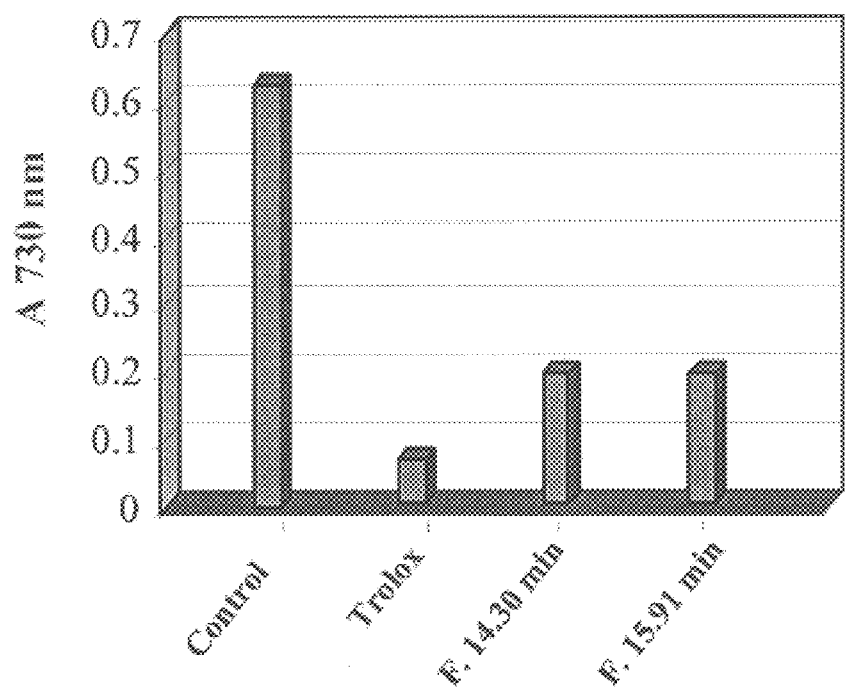
FIG. 10 is a series of bar graphs showing the antioxidative activity of HPLC isolated fractions of 13.46 and 18.08 minutes. The fractions obtained from HPLC were directly measured for antioxidative activity without equalizing concentrations.

The fractions collected showed antioxidative activity. FIG. 10 shows antioxidative activity of 13.46 min. and 18.08 min. fractions using the ABTS radical assay. Both fractions showed strong antioxidative activity in the model testing system at the concentration levels used for the assay (the concentration of peptide samples were not adjusted after HPLC isolation due to the small volume obtained), although they were not as strong as the commercial antioxidant Trolox (FIG. 10). However, since relative concentration of peptides in the two fractions was different, the relative antioxidative activities of the fractions was not determined.

EXAMPLE 9

Amino Acid Sequence Determination of HPLC Isolated Peptide using LC/MS/MS

Amino acid sequences were determined for the peptides identified in Example 8. Liquid chromatography/Mass spectrophotography (LC/MS/MS) was used for measuring the molecular weight of HPLC isolated peptides and for determining amino acid sequences. A Perkin Elmer Sciex API 365 Mass Spectrphotography apparatus was used. The following settings were used: Mass range: 20.0 to 800.0 by 0.1 amu; dwell=1.0 ms; pause =2.0 ms; 2.60 min. (29 scans) with no digestion enzyme. In order to confirm the amino acid sequence obtained by HPLC, a database search was performed of the "Medline" database using the BioMultiView 1.3.1 program search algorithm.

Figure 11:
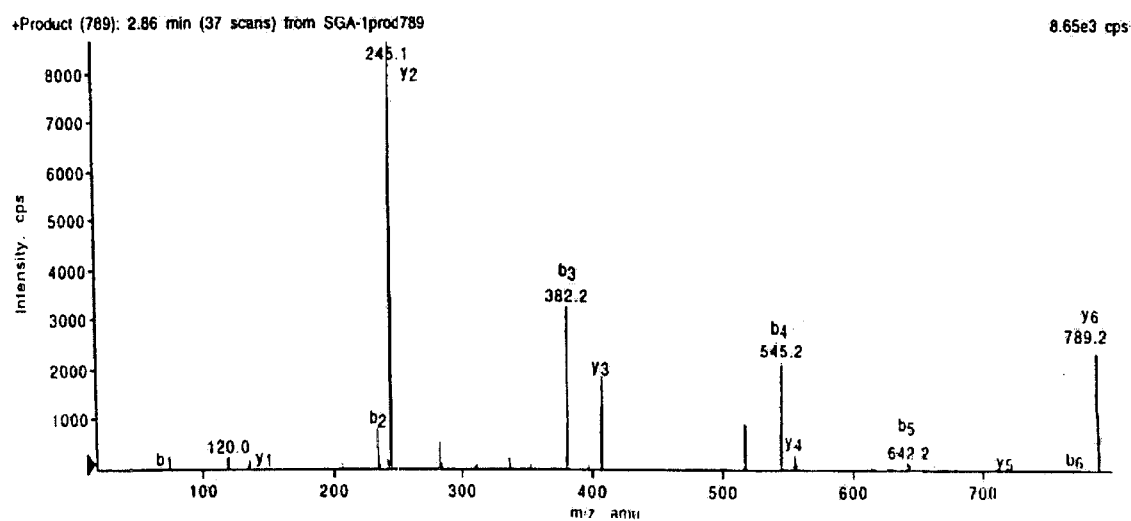
FIG. 11 shows the Liquie Chromatography/Mass Spectrometry/mass spectrometry LC/MS/MS spectra of the HPLC isolated 13.46 minute fraction.

Results of the LC/MS/MS analysis for 1 fragment generated in the MS/MS process are shown in FIG. 11. These results indicate that the fraction at 13.46 min. in HPLC spectra purified from Phase I has a molecular weight of 788.2 Dalton. Results of other LC/MS/MS fragments as well as those shown in FIG. 11, together with a database search for the amino acid sequences of milk proteins revealed that the sequence of the peptide is Ala-Tyr-Phe-Tyr-Pro-Glu (AYFYPE) (SEQ ID NO:1). The AYFYPE peptide is a fragment of alpha S1-casein (amino acid residue 158–163) from bovine milk.

The same approach was used to determine the molecular weight and amino acid sequence of the 18.08 min. fraction. Results from LC/MS/MS indicated that the peptide in fraction 18.08 min. has a molecular weight of 901.4 Dalton. Its amino acid sequence is: Leu-Ala-Tyr-Phe-Tyr-Pro-Glu (LAYFYPE) (SEQ ID NO:2) which has one more amino acid (Leu) at its N-terminus compared to the peptide in fraction 13.46 min.

EXAMPLE 10

Analysis of Antioxidative Activity of Chemically Synthesized Peptide AYFYPE

The peptide AYFYPE was chemically synthesized in order to further confirm its antioxidative activity. The total antioxidant activity and total reducing power were determined for the synthesized peptide using the ABTS total antioxidative assay and the total reducing power ABTS radical assay, respectively, as described in Example 2 above.

The peptide AYFYPE was chemically synthesized by the Peptide Synthesis Facility, University of Wisconsin Biotechnology Center using automated peptide synthesizers with Fmoc chemistry. Synthesis was carried out at a scale variable from 25 to 2000 micromole using a 2-column automated synthesizer (Applied Biosystems "Pioneer", Foster City, Calif.). The standard resin used a polyethylene glycol-polystyrene support. The resins were preloaded to an acid-labile linker with the chosen C-terminal amino acid for the production of peptide acids, or with an acid-labile amine for constructing peptide amides.

The general method of synthesis follows the principles initially described by Merrifield (Merrifield, R. B., "Solid phase peptide synthesis 1. The synthesis of a tetrapeptide," *J. Am. Chem. Soc.* 85:7129 (1963)) with modification subsequently introduced by Meienhofer et al. (Meienhofer, J., Waki, M., Heimer, E. P., Lambros, T. J., Makofske, R. C. & Chang, C-D., "Solid phase synthesis without repetitive acidolysis," *J. Peptide Protein Res.* 13:35 (1979)) and Fields et al. (Fields, C. G., Lloyd, D. H., Macdonald, R. L., Otteson, K. M. & Noble, R. L., "HBTU activation for automated Fmoc solid-phase peptide synthesis," *Peptide Res.* 4:95 (1991)). Each synthetic cycle resulted in the addition of one amino acid residue to that already linked to the resin, so that the synthesis proceeds from the C-terminal to N-terminal direction. The free amino acids were each protected at the α-amino group with Fmoc (9-fluorenymethoxycarbonyl). Reactive functional groups on amino acid side chains were also protected during synthesis to prevent undesirable side-reactions. The standard protective groups used were: Boc (butoxycarbonyl) for lysine a-amino group and tryptophan indole nitrogen; O-t-Butyl (tert. Butyl ester) for aspartic and glutamic acids carboxyl groups; t-Butyl for serine and threonine hydroxyls; Pmc (2,2,5, 7,8-Pentamethylchlorman-6-sulfonyJ) for the guanidino-N of arginine; and Trityl for cysteine sulfhydryl, histidine imidazole-N, and asparagine/glutamine amide nitrogen.

(Reagent Sources:
Preloaded synthesis resins, HATU and DIEA were purchased from Applied Biosystems, Foster City, Calif.
Fmoc amino acids were purchased from Novachem, La Jolla, Calif.
All solvents and scavengers were of synthesis or hpic grade and are purchased from various suppliers, principally Fisher, Sigma/Aldrich and Fluka.)

The ABTS total antioxidative activity assay and total reducing power assay were performed as described in Example 2. Trolox was used as a positive control and PBS buffer was used as a negative control. For the total antioxidative ABTS assay, the concentration of peptide sample was 0.0832 mM. For the ABTS radical scavenging assay, the concentration of peptide sample was 0.0832 mM. The concentration of Trolox was 0.0208 mM for both assays.

Figure 12:
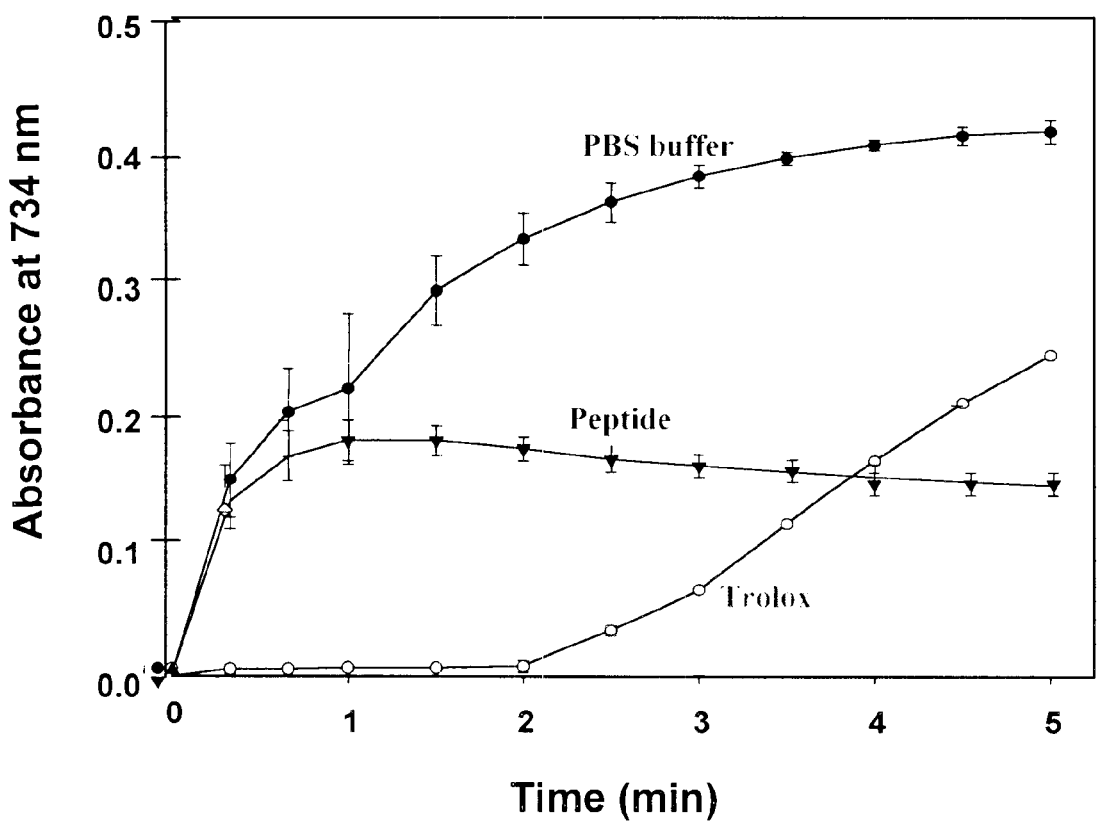
FIG. 12 is a graph showing the total antioxidative activity of peptide AYFYPE at various times after reaction initiation using an ABTS total antioxidative activity assay. The data represents mean values and standard errors of the mean (SEM) for n=5. The concentration of Trolox was 0.0208 mM and the concentration of the synthesized peptide 0.0832 mM.

Results of the total antioxidative assay indicated that the synthesized peptide AYFYPE (SEQ ID NO:1 ) has an antioxidative profile similar to that of lo the Phase I fraction (FIG. 12). As with the Phase I fraction (FIG. 2.), some oxidation was observed in samples containing AYFYPE at the earliest time points. However, this oxidation reached maximal levels within about 1.5 hours. The antioxidative activity of the synthetic peptide sample was significant ($p<0.05$) when compared to PBS controls at time points after the 1 hour time point (FIG. 12). In the presence of Trolox, on the other hand, oxidation was virtually totally suppressed until after 2 hours. The similar curves obtained for the synthesized peptide and the Phase I fraction support the conclusion that the antioxidative activity observed in the Phase I sample is mainly due to the peptide antioxidant (i.e., AYFYPE), and not other components of Phase I.

Figure 13:
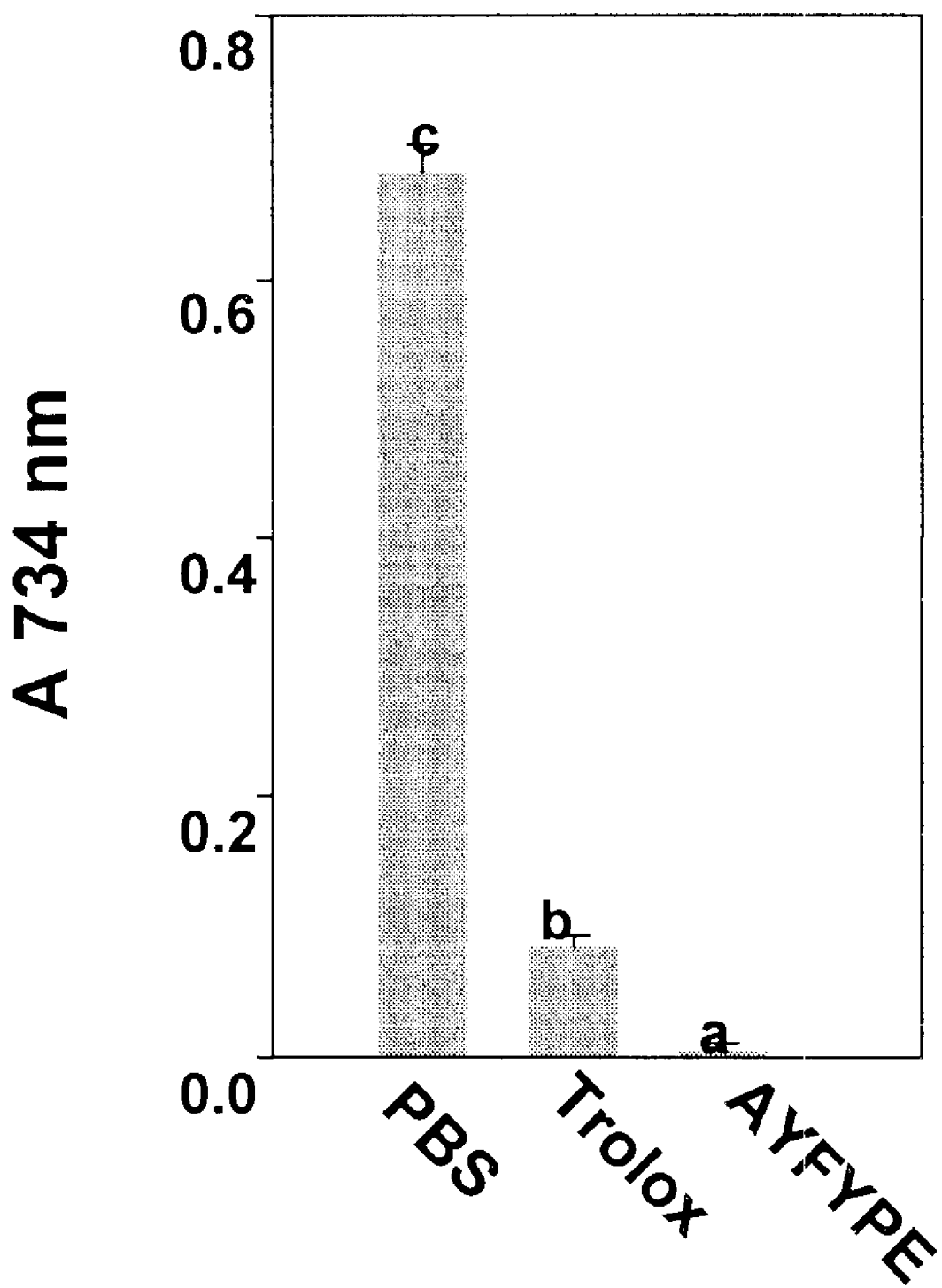
FIG. 13 is a graph showing the reducing power of peptide AYFYPE and Trolox in an ABTS radical assay. The data represents mean values and standard errors of the mean (SEM) for n=5. The concentration of Trolox was 0.0208 mM and the concentration of the synthesized peptide was 0.0832 mM.

Results of the ABTS free radical assay indicated that the synthesized peptide AYFYPE (SEQ ID NO:1) has strong antioxidative activity when measured as reducing power in terms of scavenging pre-formed ABTS radical (FIG. 13). Results for the peptide AYFYPE were statistically significant ($p<0.05$) when compared to PBS. The antioxidative activity of the peptide AYFYPE (SEQ ID NO:1) shown in this example, confirms that the antioxidative activity observed in Phase I fractions of milk proteins after cleavage with glutamyl endopeptidase is the result, at least in part, of antioxidative peptides in the fraction.

EXAMPLE 11

Antioxidative Activity of HPLC Isolated Peptides of Fractions 14.30 min. and 15.91 min. from the Phase I Fraction of Milk Proteins Cleaved with Glutamyl Endopeptidease from *Bacillus licheniformis*

An analysis was performed of antioxidative activity of two additional HPLC-separated hydrolysate fractions generated after digestion of milk proteins with glutamyl endopeptidase from *Bacillus licheniformis* (protease A from Examples 1–7). HPLC was performed as described in Example 8.

Several peaks from the HPLC experiment described in Example 8 were identified as having antioxidative activity. Fractions with peaks at 14.30 min. and 15.91 min. elution times (FIG. 9) were collected for further analysis. This analysis revealed that these two fractions have amino acid sequences that differ by only 1 amino acid. (See Example 12.) These two fractions, therefore, were analyzed together in these experiments.

Figure 14:
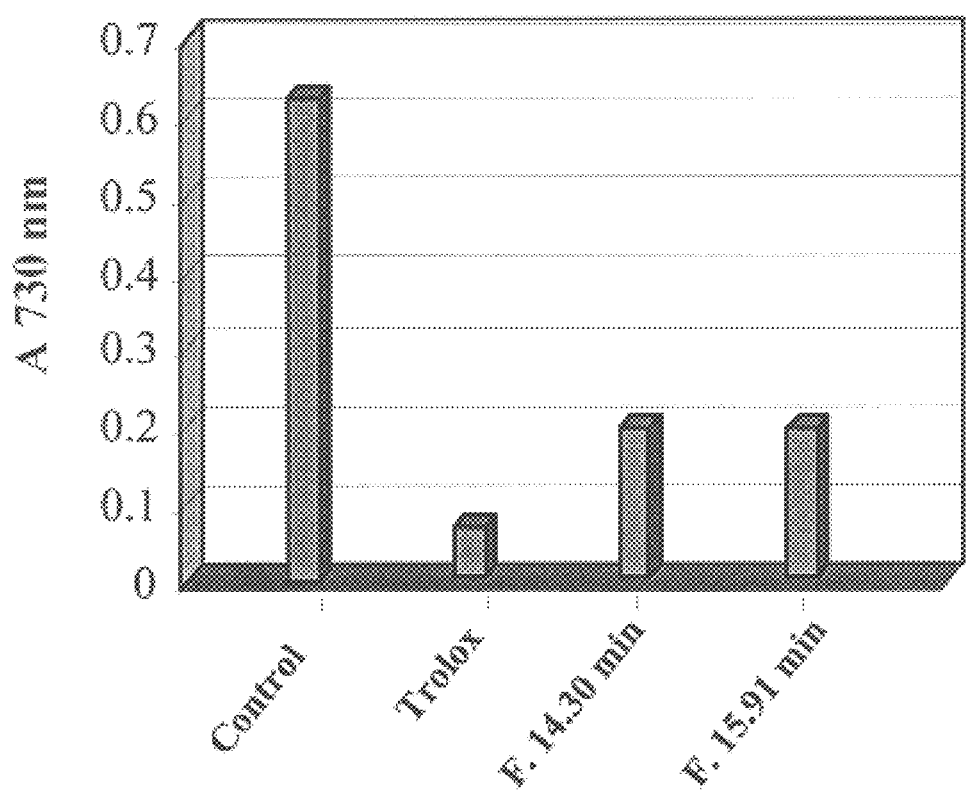
FIG. 14 is a series of bar graphs showing the antioxidative activity of HPLC-isolated fractions of 14.30 and 15.91 minutes. The fractions obtained from HPLC were directly measured for antioxidative activity without equalizing concentrations.

The 14.30 min. and 15.91 min. elution time fractions showed antioxidative activity. FIG. 14 shows antioxidative activity of peak 14.30 min. and 15.91 min. fractions using the ABTS radical assay. Both fractions showed strong antioxidative activity in the ABTS radical assay at the concentration levels used for the assay (FIG. 14). Although the antioxidative activities of the peptide fractions were not as strong as the commercial antioxidant Trolox, this may be due to a lower concentration of peptide since the concentration of peptide samples were not adjusted after HPLC isolation due to the small volume obtained.

EXAMPLE 12

Amino Acid Sequence Determination of HPLC-Isolated Peptides using LC/MS/MS

Amino acid sequences were determined for the peptides identified in Example 11 using similar mass spectrophotography techniques, as described in Example 9.

Figure 15:
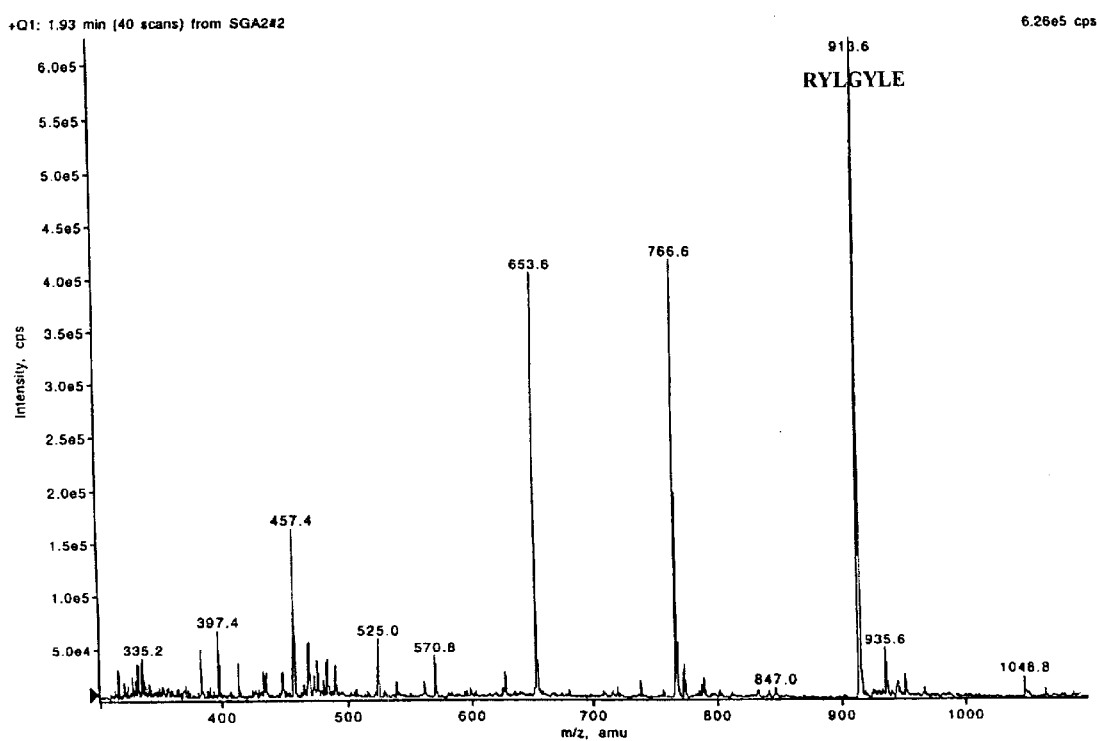
FIG. 15 shows the MS/MS spectra of the HPLC-isolated 14.30 minute fraction. The peak produced by the peptide RYLGYLE is indicated.

Results of the LC/MS/MS analysis for several fragments generated in the MS/MS process are shown in FIG. 15. Results of LC/MS/MS analysis indicates that the fractions at 14.30 min. and 15.91 min. in HPLC spectra purified from Phase I have a molecular weight of 912.6 Daltons and 756.6 Daltons, respectively. Analysis of LC/MS/MS spectra together with a database search for the amino acid sequences of milk proteins revealed that the sequence of the peptide collected from fraction 14.30 min. was Arg-Tyr-Leu-Gly-Tyr-Leu-Glu (SEQ ID NO:3) (RYLGYLE, FIG. 5), and for the peptide collected at 15.91 min. was Tyr-Leu-Gly-Tyr-Leu-Glu (SEQ ID NO:4) (YLGYLE). Both peptides are fragments of alpha S1-casein (amino acid residues 105~111/RYLGYLE and 106~111/YLGYLE, respectively) from bovine milk.

EXAMPLE 13

Analysis of Antioxidative Activity of Chemically Synthesized Peptide RYLGYLE (SEQ ID NO:4)

The peptide RYLGYLE was chemically synthesized in order to further confirm its antioxidative activity. The total antioxidant activity and total reducing power were determined using the ABTS total antioxidative assay and the total reducing power ABTS radical assay, respectively, as described in Example 2 above.

The peptide RYLGYLE (SEQ ID NO:4) was chemically synthesized as described in Example 10. The ABTS total antioxidative activity assay and total reducing power assay were performed as described in Example 2. Trolox was used as a positive control and PBS buffer was used as a negative control. For the total antioxidative ABTS assay, the concentration of peptide sample was 0.0521 mM. For this assay, the concentration of Trolox was 0.2083 mM. For the ABTS radical scavenging assay, the concentration of peptide sample was 0.0832 mM. For this assay, the concentration of Trolox was 0.0208 mM.

Figure 16:
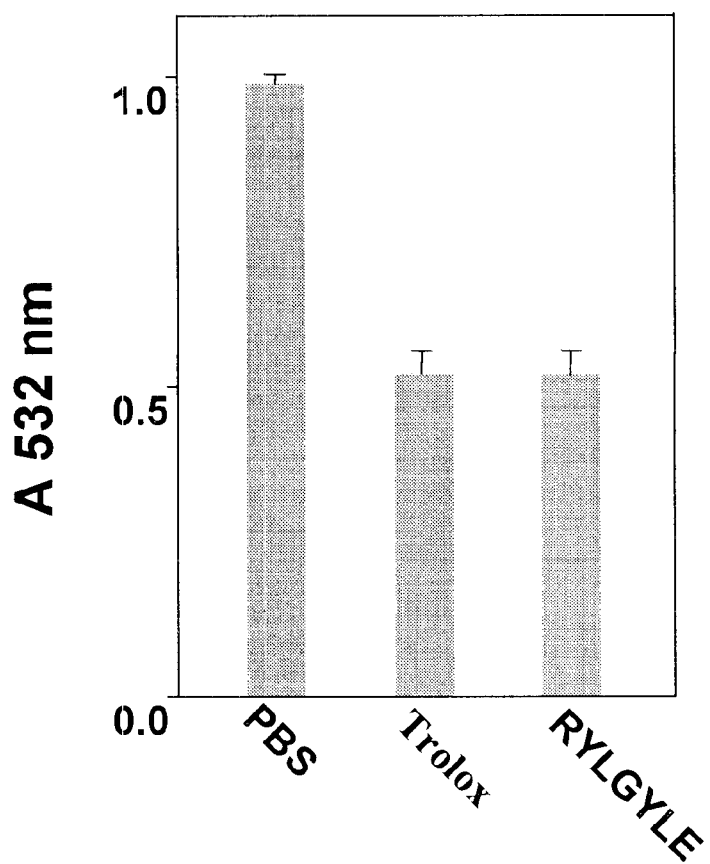
FIG. 16 is a graph showing the total antioxidative activity of peptide RYLGYLE at various times after reaction initiation using an ABTS total antioxidative activity assay. The data represents mean values and standard errors of the mean (SEM) for n=5. The concentration of Trolox for this experiment was 0.0521 mM. The concentration of the synthesized peptide was 0.2083 mM.
Figure 17:
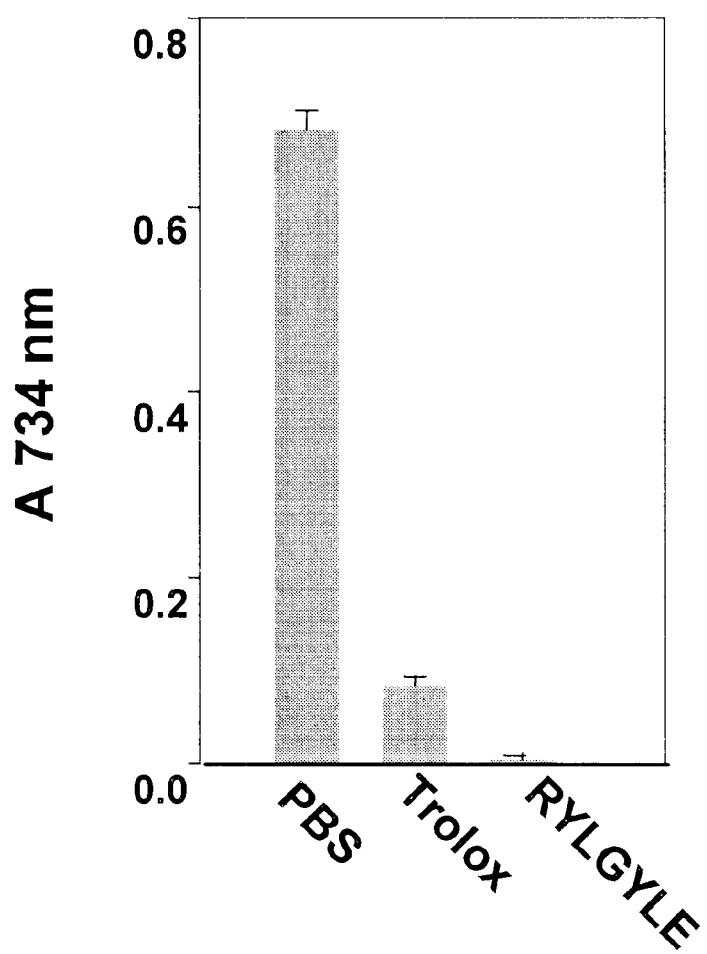
FIG. 17 is a graph showing the reducing power of peptide RYLGYLE and Trolox in an ABTS radical assay. The data represents mean values and standard errors of the mean (SEM) for n=5. The concentration of Trolox for this experiment was 0.0208 mM. The concentration of the synthesized peptide was 0.0832 mM.

Results of the total antioxidative and reducing power assays indicate that the synthesized peptide RYLGYLE (SEQ ID NO:4) has antioxidative activity. The peptide RYLGYLE (SEQ ID NO:4) has total antioxidative activity on a molar basis that is similar to that of Trolox and statistically significant ($p<0.05$) when compared to PBS (FIG. 16). Analysis of peptide RYLGYLE by the ABTS free radical scavenging assay confirmed that this peptide has antioxidative activity. This free radical scavenging activity was statistically significant when compared to PBS controls (FIG. 17). The antioxidative activity of the peptide RYLGYLE (SEQ ID NO:4) shown in this example, supports the conclusion that the antioxidative activity observed in Phase I fractions of milk proteins after cleavage with glutamyl endopeptidase is due, at least in part, to this antioxidative peptide in the fraction.

EXAMPLE 14

Antioxidative Activity of HPLC-Isolated Peptides from the Phase I Fraction of Milk Proteins Cleaved with Papain An analysis was performed of antioxidative activity of hydrolysate fractions generated after digestion of milk proteins with papain (protease D from Examples 1–7).

Samples (Phase I fractions from protein hydrolysates generated by treatment with papain as described in Example 1) were prepared for HPLC analysis by drying the sample collected from Phase I (see FIG. 1) with $N_2$ to remove acetone. The dried sample was dissolved in 1:1 (v/v) dH2O:eluent A (HPLC first mobile phase described below). The sample was mixed and centrifuged to remove precipitates before analysis by reverse phase HPLC. Reverse phase HPLC was performed using a Whatman EQC 5 µl 100A C18 (4.6'250 mm) column (Whatman, Clifton, N.J.), a Hitachi L-6200A pump, an L-4500 diode array detector, and a D6500 DAD HPLC system.

Two mobile phases (eluents) were used in the HPLC separation; the first mobile phase was 1% acetone containing 0.1% Trifluoroacetic acid (TFA), and the second mobile phase was 80% acetone containing 0.05% TFA. The HPLC flow rate was set at a rate of 0.4 ml/min. and ultraviolet absorbance of fractions was measured at 280 nm.

The gradient elution program was set as follows:
 0~20 min., from 90% first mobile phase/10% second mobile phase to 70% first mobile phase/30% second mobile phase
 20~25 min., from 70% first mobile phase/30% second mobile phase to 50% first mobile phase/50% second mobile phase
 25~26 min., from 50% first mobile phase/50% second mobile phase to 100% second mobile phase
 26~35 min., with 100% second mobile phase.

Antioxidative activity of the fractionated 280 nm absorbance peaks from HPLC was measured using the ABTS radical assay as described in Example 2 above.

Figure 18:
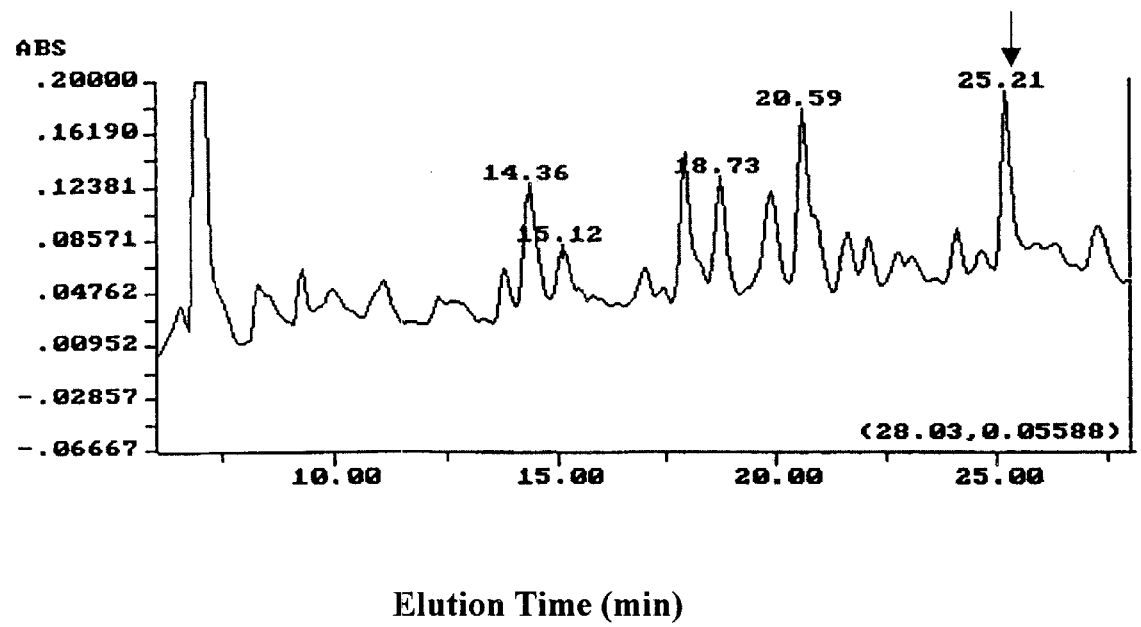
FIG. 18 is an HPLC chromatograph of peptides separated from Phase I fractions generated according to the method for isolating antioxidative peptides shown schematically in FIG. 1 and described in detail in Example 1. Papain was used as the protease. Peptides of fraction of elution time 25.21 minutes are discussed in Examples 14 through 16.

FIG. 18 shows the HPLC chromatograph of protein hydrolysates obtained from Phase I of the papain digested samples (see Example 1). Several peptides were isolated from this phase. The main peptide peak at 25.21 min. elution time was collected for further analysis. This peptide is highly hydrophobic according to its HPLC elution profile since it eluted at greater than 50% eluent B, which contained 80% acetone and 0.05% TFA.

Figure 19:
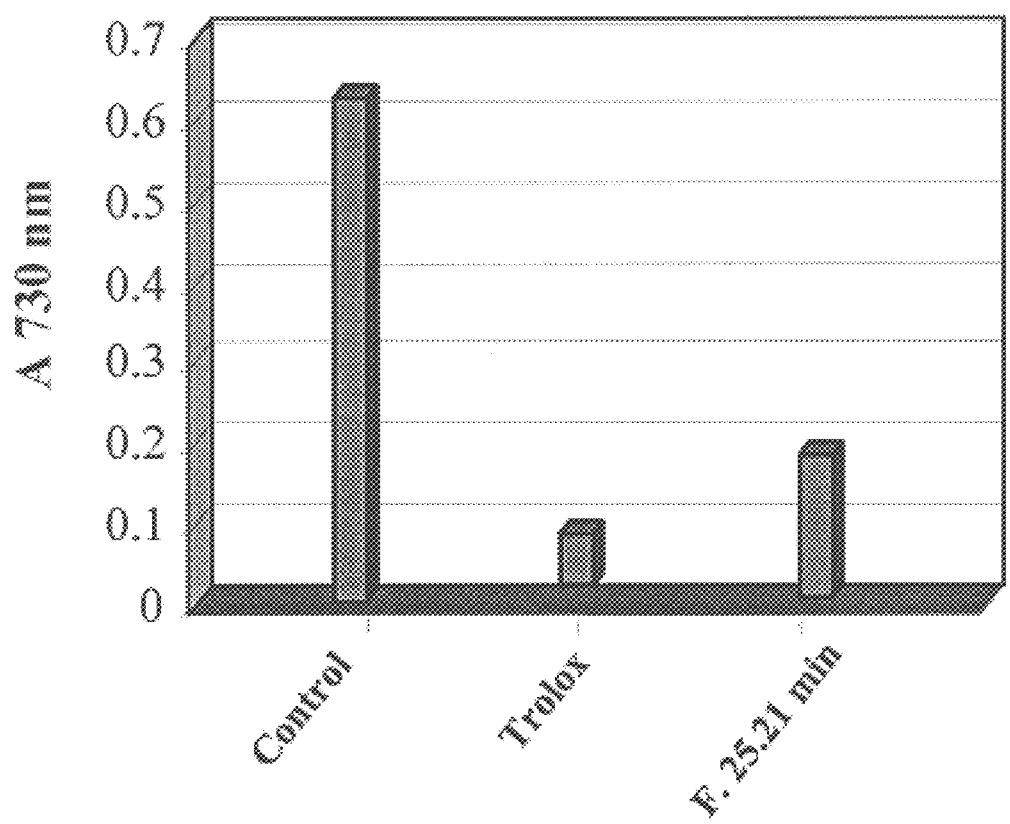
FIG. 19 is a series of bar graphs showing the antioxidative activity of the 25.21 minute HPLC fraction. This fraction was directly measured for antioxidative activity without adjusting concentrations to match that of Trolox.

The 25.21 min. fraction showed antioxidative activity. FIG. 19 shows the antioxidative activity of peak 25.21 min. according to the ABTS radical assay, as well as the activity of the positive control, Trolox, and the negative control, PBS. This fraction showed strong antioxidative activity in the ABTS radical scavenging assay at the concentrations used for the assay. Although the activity at the concentration of peptide used in the assay was not as strong as the activity of the commercial antioxidant Trolox (FIG. 19), a comparison of the relative strength of the peptide vis-a-vis Trolox cannot be made here since the concentration of peptide samples were not adjusted after HPLC isolation due to the small volume obtained.

EXAMPLE 15

Amino Acid Sequence Determination of HPLC Isolated Peptide using MS/MS

The amino acid sequence was determined for the peptide identified in Example 14 using Mass spectrophotographic techniques as described in Example 9.

Figure 20:
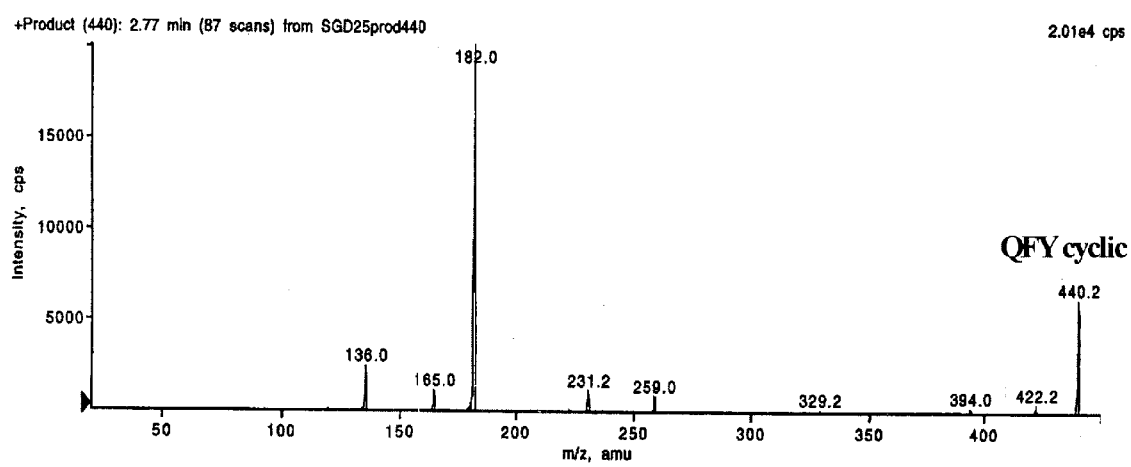
FIG. 20 shows the MS/MS spectra of the HPLC isolated 25.21 minute fraction. The peak produced by the cyclic QFY peptide is indicated.

Results of the LC/MS/MS analysis for several fragments generated in the LC/MS/MS process are shown in FIG. 20. The peak at M/Z=440.2 did not completely match any amino acid sequence reported for milk proteins when a database search was performed. Further studies revealed that the peptide in this peak was a cyclic tripeptide Gln-Phe-Tyr (QFY) (SEQ ID NO-5), especially under the condition of LC/MS/MS measurement. The amine group (—CONH2) in the glutamine residue at the N-terminus of the QFY peptide spontaneously forms a co-valent linkage with the carboxylic acid of tyrosine at the C-terminus, forming a cyclic structure that corresponds to the peak with M/Z=440.2. The linear form of QFY was never detected by LC/MS/MS. The peptide is a fragment of alpha S1-casein (amino acid residues 167–169) from bovine milk. The peak at M/Z=182.0 in FIG. 20 is the phenylanine residue in QFY.

EXAMPLE 16

Analysis of Antioxidative Activity of Chemically Synthesized Peptide QFY

An analysis was performed of the antioxidative activity of both linear and cyclic chemically-synthesized forms of the peptide QFY. The total antioxidant activity, superoxide anion hydroxyl radical quenching capacity, and total reducing power were determined using the ABTS total antioxidative assay, hydroxyl radical quenching assay, and the total reducing power ABTS radical assay, respectively, as described in Examples 2 and 7 above.

Both linear and cyclic QFY peptides were chemically synthesized in order to further confirm the sequence analysis in Example 15 and to confirm their antioxidative capacity. The peptides were synthesized by the Peptide Synthesis Facility, University of Wisconsin Biotechnology Center using automated peptide synthesizers with Fmoc chemistry using standard peptide synthesis methods as described in Example 10.

The antioxidative activity of the synthesized peptides was determined using three different assays. The ABTS total antioxidative activity assay and total reducing power assay were performed as described in Example 2. The superoxide anion hydroxyl radical quenching capacity (i.e., Fenton) assay was performed as described in Example 7. As in previous examples, Trolox was used as a positive control and PBS buffer was used as a negative control. For the total antioxidative ABTS assay, the concentration of peptide sample was 0.0832 mM and the concentration of Trolox was 0.0208 mM. For the superoxide anion hydroxyl radical quenching assay, the concentration of sample was 0.2083 mM for both cyclic and linear forms and the concentration of Trolox was 0.0521 mM. For the ABTS radical scavenging total reducing power assay, the concentration of peptide sample was 0.0832 mM and the concentration of Trolox was 0.0208 mM. Data are indicated as mean and SEM of 5 replicates for all assays.

Figure 21:
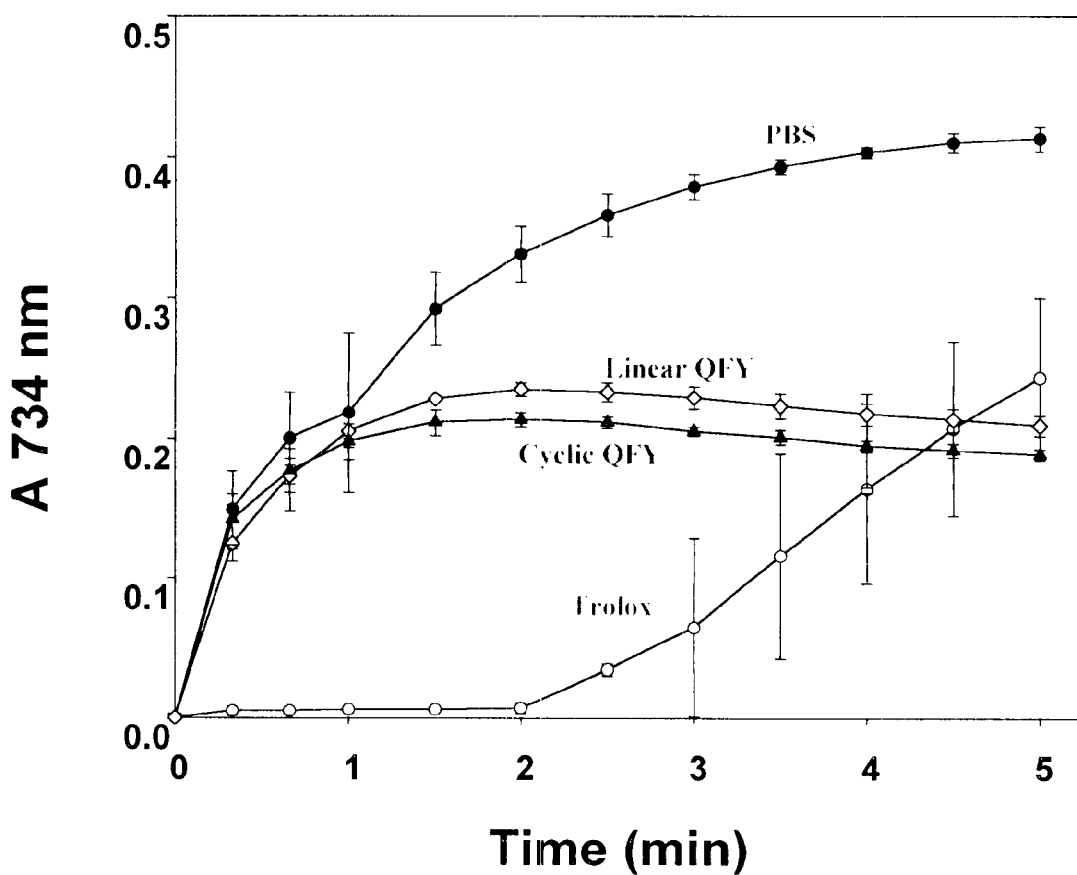
FIG. 21 is a graph showing the total antioxidative activity of cyclic and linear synthetic QFY peptides at various times after reaction initiation using an ABTS total antioxidative activity assay. The data represents mean values and standard errors of the mean (SEM) for n=5. The concentration of Trolox for this experiment was 0.0208 mM: The concentration of both linear and cyclic QFY peptides was 0.0832 mM.

Results of the total antiodixative assay indicate that the synthesized linear and cyclic peptide QFY (SEQ ID NO:5) have antioxidative profiles similar to that of Phase IV. The cyclic form of QFY had slightly stronger antioxidative activity according to the results shown in FIG. 21. As with Phase IV (FIG. 2.), some oxidation was observed in samples containing QFY at the earliest time points. However, this oxidation reached maximal levels within about 1.5 hours, after which point it was significantly reduced ($p<0.05$) when compared to PBS controls (FIG. 20). In the presence of Trolox, on the other hand, oxidation was virtually totally suppressed until after 2 hours. The similar curves obtained for the synthesized peptide and the Phase I sample support the conclusion that the antioxidative activity observed in the Phase I sample is a property of a peptide antioxidant (i.e., cyclic QFY) and not other components of Phase I. Additionally, the results indicate that both the linear and cyclic forms of the peptide QFY have antioxidative activity.

Figure 22:
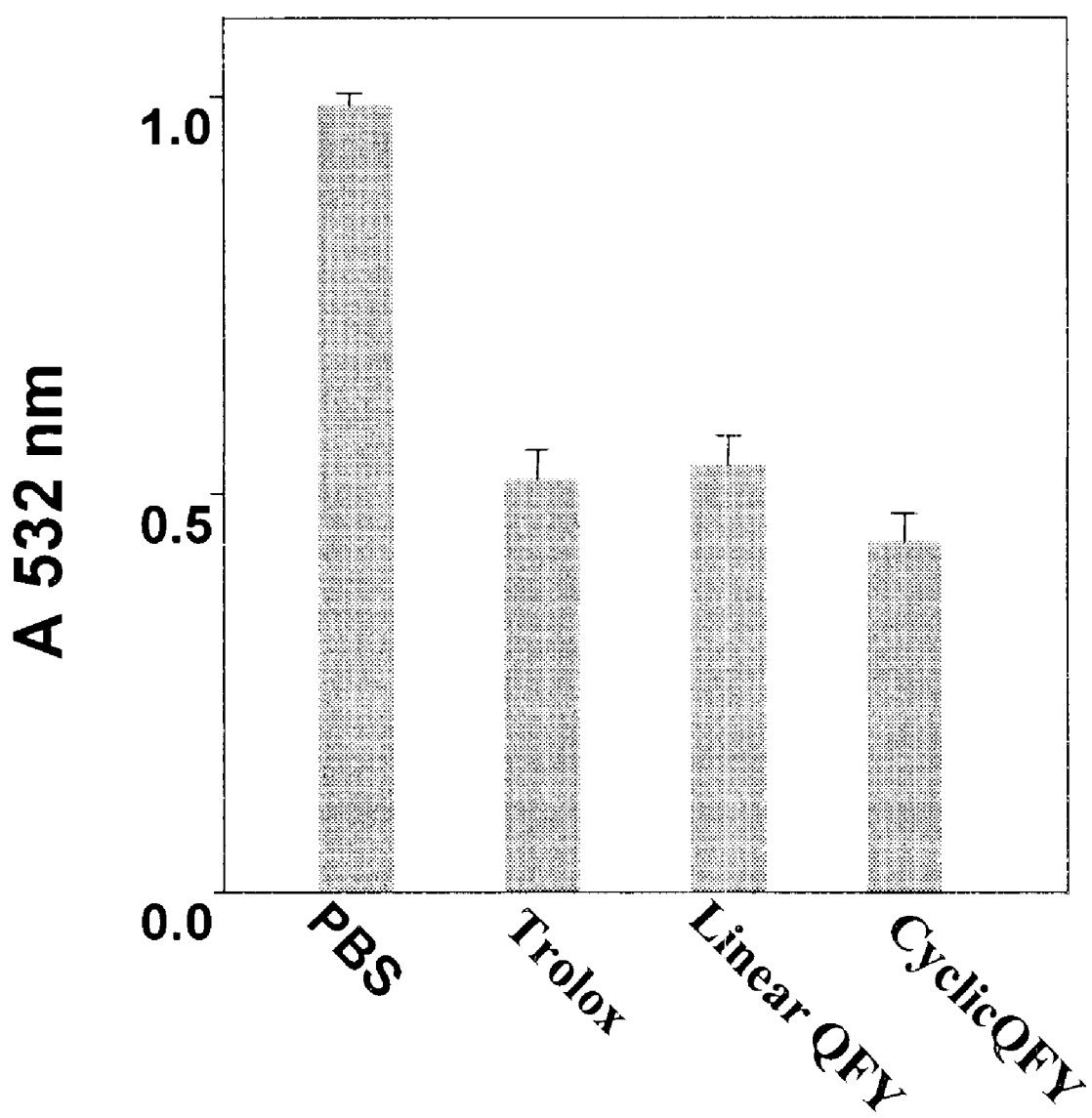
FIG. 22 is a graph showing the hydroxyl radical quenching capacity of the linear and cyclic QFY peptides, PBS, and Trolox in a superoxide anion assay. The data represents mean values and standard errors of the mean (SEM) for n=5. The concentration of Trolox for this experiment was 0.0521 mM. The concentration of linear and cyclic QFY was 0.2083 mM.

Analysis of the linear and cyclic QFY peptide by the superoxide anion hydroxyl radical assay also support the conclusion that these peptides have antioxidative activity and indicate that these peptides are effective in quenching superoxide anion hydroxyl radicals. As shown in FIG. 22, both forms of the peptide QFY possess the capacity to quench hydroxyl radicals in the superoxide anion assay. This capacity was statistically significant when compared to the PBS control. The cyclic form of QFY had a slightly stronger capacity to quench hydroxyl radicals, compared to the linear form of QFY. The hydroxyl radical is an exceptionally active agent that can react nonselectively with organic constituents of food. Consequently, it can directly initiate lipid oxidation in food systems. Therefore, results of this assay indicate that the cyclic and linear peptides QFY would be effective at preventing oxidation in food systems.

Figure 23:
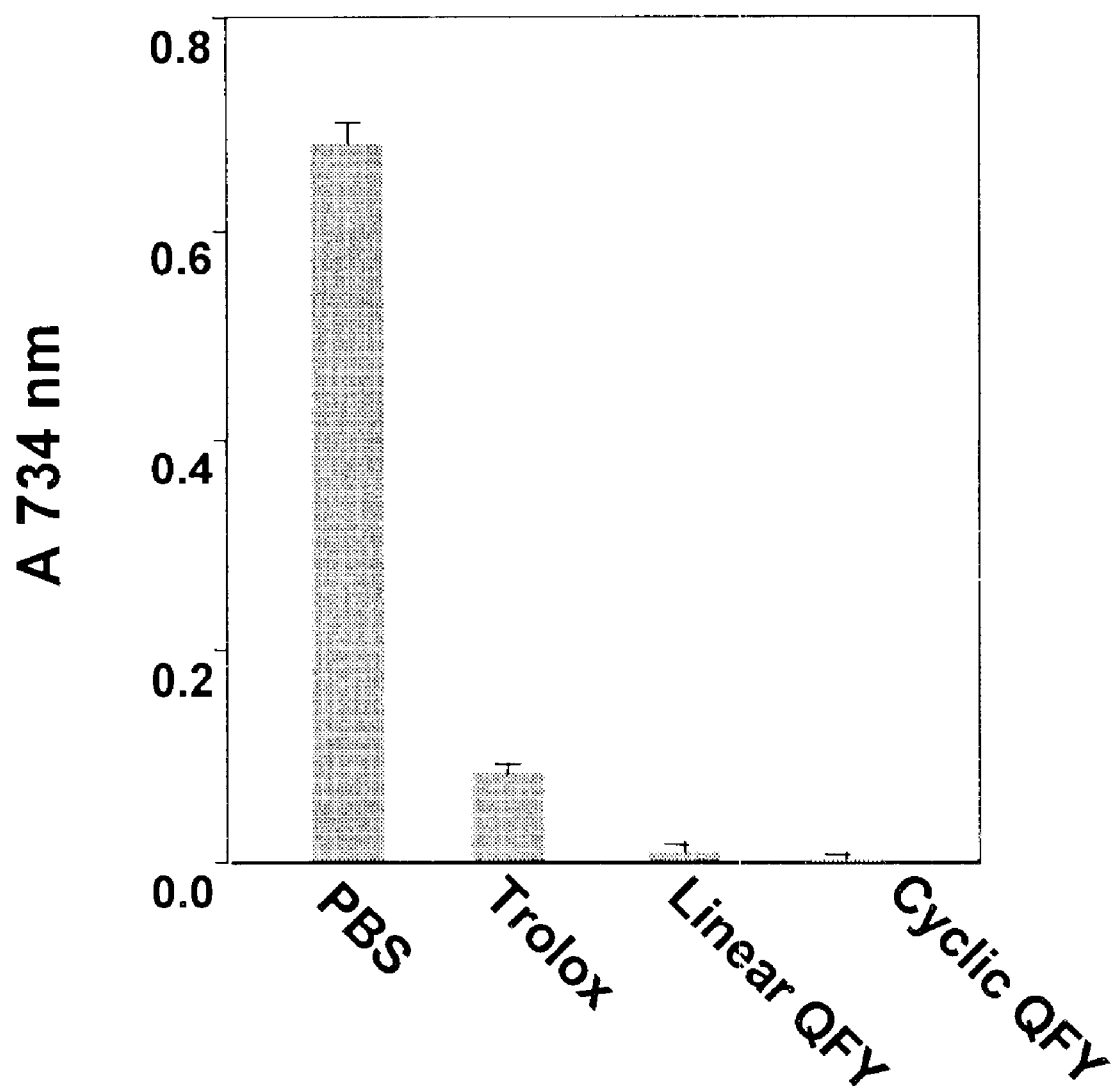
FIG. 23 is a graph showing the reducing power of the linear and cyclic QFY peptides, PBS, and Trolox in an ABTS radical assay. The data represents mean values and standard errors of the mean (SEM) for n=5. The concentration of Trolox for this experiment was 0.0208 mM. For both linear and cyclic QFY the concentration was 0.0832 mM.

Analysis of chemically-synthesized linear and cyclic peptide QFY (SEQ ID NO:5) by the ABTS free radical assay confirm that these peptides have strong antioxidative activity. As shown in FIG. 23, both linear and cyclic forms of the peptide QFY significantly ($p<0.05$) scavenged pre-formed ABTS radical in this assay when compared to PBS. The antioxidative activity of the peptide QFY (SEQ ID NO:5) shown in this example, further supports the conclusion that the antioxidative activity observed in Phase IV fractions of milk proteins after cleavage with papain is the result, at least in part, of antioxidative QFY peptides in the fraction.

EXAMPLE 17

Preparation of Peptide Antioxidant Fractions From Soy Protein Isolate

Soy protein isolate was subjected to the separation procedure of FIG. 1, as described in Example 1 above, to prepare peptide antioxidant fractions from soy protein isolate.

The process was carried out essentially as described in Example 1. Seven hundred grams of soy protein isolate (SPI, SuproXT 34, Protein echnology International, St. Louis, Mo.) suspended in 4300 g of hot ater (about 60° C.) was used in step 1. The protease reaction mixture was eated to 83° C. to inactivate protease enzymes.

Leucine was used as a standard for determining the concentration of peptides using the trinitrobenzene sulfonic acid (TNBS) method described in Example 1. PBS was use as negative control. The total antioxidative activity of soy protein hydrolysate is expressed as Trolox equivalent, indicating their relative antioxidative capacity per equimolar level of Trolox. The ABTS total reducing power assay was performed as described in Example 2.

Figure 24:
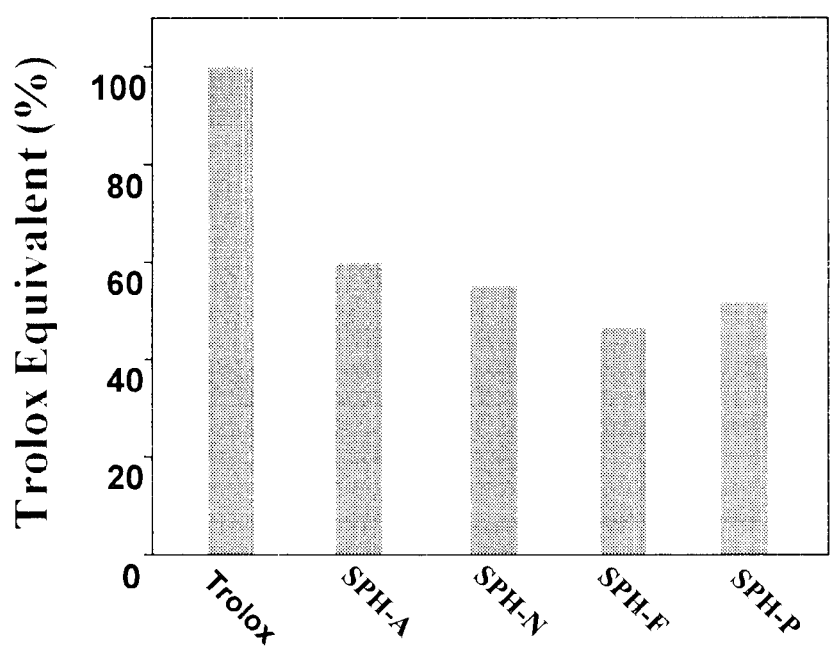
FIG. 24 is a graph of total antioxidant activity of Phase I fractions of soy protein hydrolysate extracts prepared as described schematically in FIG. 1 and in detail in Example 1, except that soy protein was used in placed of milk protein. The bars represent fractions generated by different proteases as described below. Total antioxidant activity (reducing power in terms of scavenging pre-formed ABTS radical) is expressed as Trolox equivalents (defined as the relative antioxidative activity of the peptide sample compared to an equal molar level of Trolox). Data are mean values of duplicate measurements. SPH-A: Soy protein isolate treated with Alcalase (NOVO Nordisk, Bagsvaerd, Denmark); SPH-N: Soy protein isolate treated with Neutrase (NOVO Nordisk); SPH-F: Soy protein isolate treated with Flavozyme (NOVO Nordisk); SPH-P: Soy protein isolate treated with Promod 24 L (Biocatalysts Ltd., Mid Glamorgan, UK).

The soy protein peptide fractions in Phase I produced according to the general scheme of FIG. 1 contained antioxidative peptides. Soy protein peptide fractions were produced by proteolytically cleaving soy proteins and processing the resulting peptide fractions according to the scheme shown in FIG. 1. As shown in FIG. 24, these fractions possessed antioxidative activity for all of the proteases tested. This activity was greater than that observed with the negative PBS control (Trolox equivalent value=0). These data indicate that the antioxidant peptide preparation scheme shown in FIG. 1 can be used with other protein preparations besides non fat dried milk proteins.

EXAMPLE 18

Preparation of Peptide Antioxidant Fractions From Whey Protein Isolate

Whey protein isolate was subjected to the separation procedure of FIG. 1 to prepare peptide antioxidant fractions from soy protein isolate.

Using the process essentially described in Example 1, ten grams of whey protein powder (Alacen 841, New Zealand Milk Products, Wellington, New Zealand, containing 80% proteins) prepared in 90 g of hot water (about 60° C.) was used in step 1. Papain (Papain 6000, Valley Research Inc., Hammond, Ind.) was used as the protease in the peptide preparation procedure. The ABTS total reducing power assay was performed as in Example 2.

The whey protein peptide fractions in Phase I produced according to the general scheme of FIG. 1 contain antioxidative peptides. Whey protein peptide fractions were produced by proteolytically cleaving whey proteins with papain and processing the resulting peptide fractions according to the scheme shown in FIG. 1. As shown in Table 3, as with milk and soy protein preparations, peptides in the resulting Phase I fraction possess antioxidative activity in terms of their capacity to scavenge pre-formed ABTS radicals. The reduced absorbance reading at 734 nm compared to the control value, indicates that about 45% of pre-formed ABTS radical were scavenged by the added peptides from whey protein hydrolysates. These data support the conclusion that the antioxidant peptide preparation scheme shown in FIG. 1 can be used with other protein preparations in addition to non fat dried milk proteins and soy proteins.

TABLE 3

| Antioxidative capacity of whey protein hydrolysate* | | |
| --- | --- | --- |
| Sample | PBS Control | Peptides in Phase I |
| A 734 nm | 0.643 | 0.356 |

*Data are mean value of duplicated measurements.

What is claimed is:

1. An isolated peptide consisting of SEQ ID NO:5.

2. A food supplement, comprising: an antioxidative peptide selected from the group consisting of SEQ ID NO:3, SEQ ID NO:4, and SEQ ID NO:5, said antioxidative peptide being present in an amount effective for preventing in vivo oxidation; and an orally-ingestive diluent or carrier.

3. A food supplement according to claim 2, wherein the amino acid sequence is SEQ ID NO:3.

4. A food supplement according to claim 2, wherein the amino acid sequence is SEQ ID NO:4.

5. A food supplement according to claime 2, wherein the amino acid sequence is SEQ ID NO:5.

6. The food supplement according to claim 2, wherein the orally-ingestible diluent or carrier is a food product.

7. A method for identifying an antioxidative peptide from a mixture of peptides comprising:
   a) generating a mixture of peptides suspected of containing an antioxidative peptide;
   b) separating the peptides using a phase separation step which is carried out by adding an organic solvent to a solution containing the mixture of peptides, to form at least two fractions;
   c) assessing the fractions for antioxidative activity; and
   d) substantially purifying the antioxidative peptide or peptides having antioxidative activity from the fractions having antioxidative activity.

8. The method of claim 2, wherein the mixture of peptides are generated by proteolytic cleavage of a protein.

9. The method of claim 8, wherein a supernatant and a precipitate are formed during the phase separation step.

10. The method of claim 9, wherein the step of separating further comprises a salting-out process by adding salts to the supernatant to form an upper layer and a lower layer, wherein the upper layer is the first fraction and the lower layer is the second fraction.

11. The method of claim 10, wherein the fraction with antioxidative activity is the first fraction.

12. The method of claim 7, wherein the mixture of peptides is generated by proteolytic cleavage of a protein selected from milk protein, soy protein, and whey protein.

13. The method of claim 12, wherein the mixture of peptides are generated by proteolytic cleavage of milk protein.

14. The method of claim 7, wherein fractions having antioxidative activity are subjected to affinity chromatography, ion exchange chromatography, filtration, electrophoresis, hydrophobic interaction chromatography, gel filtration chromatography, reverse phase chromatography, concanavalin A chromatography, chromatofocusing, or differential solubilization to substantially purify the antioxidative peptide or peptides.

15. The method of claim 7, wherein fractions having antioxidative activity are subjected to reverse-phase HPLC to substantially purify the antioxidative peptide or peptides.

16. An isolated peptide consisting of SEQ ID NO:2.

17. A food supplement, comprising:

an antioxidative peptide consisting of SEQ ID NO:2, said antioxidative peptide being present in an amount effective for preventing in vivo oxidation; and an orally-ingestible diluent or carrier.

* * * * *

UNITED STATES PATENT AND TRADEMARK OFFICE
CERTIFICATE OF CORRECTION

PATENT NO. : 6,465,432 B1
DATED : October 15, 2002
INVENTOR(S) : Han et al.

It is certified that error appears in the above-identified patent and that said Letters Patent is hereby corrected as shown below:

<u>Title page, Item [54] and Column 1, line 1,</u>
Change "FORM" to -- FROM --.

<u>Title page,</u>
Item [73], Assignee, change "Food" to -- Foods --.

<u>Column 47,</u>
Line 50, after "comprising" begin new paragraph.
Line 54, after "and" begin new paragraph.
Line 58, change "claime" to -- claim --.

<u>Column 48,</u>
Line 55, change "2" to -- 7 --.

Signed and Sealed this

Twentieth Day of May, 2003

JAMES E. ROGAN
*Director of the United States Patent and Trademark Office*

SEQUENCE LISTING

```
<160> NUMBER OF SEQ ID NOS:  17

<210> SEQ ID NO 1
<211> LENGTH: 6
<212> TYPE: PRT
<213> ORGANISM: Bovine

<400> SEQUENCE: 1

Ala Tyr Phe Tyr Pro Glu
 1               5

<210> SEQ ID NO 2
<211> LENGTH: 7
<212> TYPE: PRT
<213> ORGANISM: Bovine

<400> SEQUENCE: 2

Leu Ala Tyr Phe Tyr Pro Glu
 1               5

<210> SEQ ID NO 3
<211> LENGTH: 6
<212> TYPE: PRT
<213> ORGANISM: Bovine

<400> SEQUENCE: 3

Tyr Leu Gly Tyr Leu Glu
 1               5

<210> SEQ ID NO 4
<211> LENGTH: 7
<212> TYPE: PRT
<213> ORGANISM: Bovine

<400> SEQUENCE: 4

Arg Tyr Leu Gly Tyr Leu Glu
 1               5

<210> SEQ ID NO 5
<211> LENGTH: 3
<212> TYPE: PRT
<213> ORGANISM: Bovine

<400> SEQUENCE: 5

Gln Phe Tyr
 1
```

```
<210> SEQ ID NO 6
<211> LENGTH: 18
<212> TYPE: DNA
<213> ORGANISM: Bovine

<400> SEQUENCE: 6
gcctacttct accctgag                                                18

<210> SEQ ID NO 7
<211> LENGTH: 21
<212> TYPE: DNA
<213> ORGANISM: Bovine

<400> SEQUENCE: 7
ctggcctact tctaccctga g                                            21

<210> SEQ ID NO 8
<211> LENGTH: 18
<212> TYPE: DNA
<213> ORGANISM: Bovine

<400> SEQUENCE: 8
tacctgggtt atctggaa                                                18

<210> SEQ ID NO 9
<211> LENGTH: 21
<212> TYPE: DNA
<213> ORGANISM: Bovine

<400> SEQUENCE: 9
cgttacctgg gttatctgga a                                            21

<210> SEQ ID NO 10
<211> LENGTH: 9
<212> TYPE: DNA
<213> ORGANISM: Bovine

<400> SEQUENCE: 10 caattctac                                                           9

<210> SEQ ID NO 11
<211> LENGTH: 9
<212> TYPE: DNA
<213> ORGANISM: Artificial Sequence
<220> FEATURE:
<223> OTHER INFORMATION: Encodes QFY peptide

<400> SEQUENCE: 11 caattttac                                                           9

<210> SEQ ID NO 12
<211> LENGTH: 9
<212> TYPE: DNA
<213> ORGANISM: Artificial Sequence
<220> FEATURE:
<223> OTHER INFORMATION: Encodes QFY peptide

<400> SEQUENCE: 12 caattctat                                                           9

<210> SEQ ID NO 13
<211> LENGTH: 9
<212> TYPE: DNA
<213> ORGANISM: Artificial Sequence
<220> FEATURE:
```

```
<223> OTHER INFORMATION: Encodes QFY peptide

<400> SEQUENCE: 13 caattttat                                                              9

<210> SEQ ID NO 14
<211> LENGTH: 9
<212> TYPE: DNA
<213> ORGANISM: Artificial Sequence
<220> FEATURE:
<223> OTHER INFORMATION: Encodes QFY peptide

<400> SEQUENCE: 14 cagttttat                                                              9

<210> SEQ ID NO 15
<211> LENGTH: 9
<212> TYPE: DNA
<213> ORGANISM: Artificial Sequence
<220> FEATURE:
<223> OTHER INFORMATION: Encodes QFY peptide

<400> SEQUENCE: 15 cagttttac                                                              9

<210> SEQ ID NO 16
<211> LENGTH: 9
<212> TYPE: DNA
<213> ORGANISM: Artificial Sequence
<220> FEATURE:
<223> OTHER INFORMATION: Encodes QFY peptide

<400> SEQUENCE: 16 cagttctat                                                              9

<210> SEQ ID NO 17
<211> LENGTH: 9
<212> TYPE: DNA
<213> ORGANISM: Artificial Sequence
<220> FEATURE:
<223> OTHER INFORMATION: Encodes QFY peptide

<400> SEQUENCE: 17 cagttctac                                                              9
```